United States Patent
Jarc et al.

(10) Patent No.: US 11,751,957 B2
(45) Date of Patent: *Sep. 12, 2023

(54) SURGICAL SYSTEM WITH TRAINING OR ASSIST FUNCTIONS

(71) Applicant: Intuitive Surgical Operations, Inc., Sunnyvale, CA (US)

(72) Inventors: Anthony M. Jarc, Duluth, GA (US); Chi Zhang, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 262 days.

This patent is subject to a terminal disclaimer.

(21) Appl. No.: 17/137,342

(22) Filed: Dec. 29, 2020

(65) Prior Publication Data

US 2021/0186634 A1  Jun. 24, 2021

Related U.S. Application Data

(63) Continuation of application No. 15/772,531, filed as application No. PCT/US2016/061694 on Nov. 11, 2016, now Pat. No. 10,912,619.

(Continued)

(51) Int. Cl.
*G09B 23/28* (2006.01)
*A61B 34/35* (2016.01)
(Continued)

(52) U.S. Cl.
CPC .............. *A61B 34/35* (2016.02); *A61B 34/10* (2016.02); *A61B 34/25* (2016.02); *A61B 34/37* (2016.02);
(Continued)

(58) Field of Classification Search
CPC ................................ G09B 23/28; G09B 23/30
See application file for complete search history.

(56) References Cited

U.S. PATENT DOCUMENTS

| | | |
|---|---|---|
| 4,887,222 A | 12/1989 | Miyake et al. |
| 5,704,791 A | 1/1998 | Gillio |

(Continued)

FOREIGN PATENT DOCUMENTS

| | | |
|---|---|---|
| CA | 2929282 A1 | 5/2015 |
| CN | 102362302 A | 2/2012 |

(Continued)

OTHER PUBLICATIONS

Reiley C.E., et.al., "Motion Generation of Robotic Surgical Tasks: Learning from Expert Demonstrations," Annual International Conference of the IEEE Engineering in Medicine and Biology, 2010, pp. 1-9.

(Continued)

*Primary Examiner* — Kurt Fernstrom
(74) *Attorney, Agent, or Firm* — SCHWEGMAN LUNDBERG & WOESSNER, P.A.

(57) ABSTRACT

Systems, methods, and tangibly-implemented software instructions for supporting a teleoperated surgical system (TSS). A surgical input that includes monitored events of the TSS, is received. A current stage of the surgical procedure is autonomously determined based on the surgical input. A call for surgeon assistance may be detected, in response to which context-relevant assistance may be provided to a surgeon console of the TSS, the context-relevant assistance being stage-synchronized with the surgical procedure.

4 Claims, 19 Drawing Sheets

Related U.S. Application Data

(60) Provisional application No. 62/374,670, filed on Aug. 12, 2016, provisional application No. 62/254,556, filed on Nov. 12, 2015.

(51) Int. Cl.
    *A61B 34/10*     (2016.01)
    *A61B 34/37*     (2016.01)
    *G16H 50/50*     (2018.01)
    *A61B 34/00*     (2016.01)
    *G16H 20/30*     (2018.01)
    *G16H 40/67*     (2018.01)
    *A61B 90/00*     (2016.01)
    *G09B 23/30*     (2006.01)
    *G16H 40/20*     (2018.01)

(52) U.S. Cl.
CPC ............ *A61B 90/361* (2016.02); *A61B 90/37* (2016.02); *G09B 23/285* (2013.01); *G09B 23/30* (2013.01); *G16H 20/30* (2018.01); *G16H 40/67* (2018.01); *G16H 50/50* (2018.01); *A61B 2034/101* (2016.02); *A61B 2034/104* (2016.02); *A61B 2034/105* (2016.02); *A61B 2034/254* (2016.02); *A61B 2034/256* (2016.02); *G16H 40/20* (2018.01)

(56) References Cited

U.S. PATENT DOCUMENTS

| | | |
|---|---|---|
| 5,769,640 A | 6/1998 | Jacobus et al. |
| 6,074,213 A | 6/2000 | Hon |
| 6,573,889 B1 | 6/2003 | Georgiev |
| 7,236,618 B1 | 6/2007 | Chui et al. |
| 8,317,744 B2 | 11/2012 | Kirschenman |
| 8,663,122 B2 | 3/2014 | Schecter |
| 8,992,230 B2 | 3/2015 | Tuchschmid |
| 9,161,817 B2 | 10/2015 | Olson et al. |
| 9,196,176 B2 | 11/2015 | Hager et al. |
| 9,268,915 B2 | 2/2016 | Holmes et al. |
| 9,341,704 B2 | 5/2016 | Picard et al. |
| 9,652,591 B2 | 5/2017 | Moctezuma De La Barrera et al. |
| 10,912,619 B2 | 2/2021 | Jarc et al. |
| 11,058,501 B2 | 7/2021 | Tokarchuk et al. |
| 2003/0029463 A1 | 2/2003 | Niemeyer |
| 2003/0216715 A1 | 11/2003 | Moll et al. |
| 2004/0106916 A1 | 6/2004 | Quaid et al. |
| 2006/0142657 A1 | 6/2006 | Quaid et al. |
| 2009/0017430 A1 | 1/2009 | Muller-Daniels et al. |
| 2009/0036775 A1 | 2/2009 | Ikuma et al. |
| 2009/0036902 A1 | 2/2009 | DiMaio et al. |
| 2009/0088634 A1 | 4/2009 | Zhao et al. |
| 2010/0191071 A1 | 7/2010 | Anderson et al. |
| 2010/0248200 A1 | 9/2010 | Ladak et al. |
| 2011/0046476 A1 | 2/2011 | Cinquin et al. |
| 2011/0267450 A1 | 11/2011 | Pronkine |
| 2011/0295247 A1 | 12/2011 | Schlesinger et al. |
| 2011/0305379 A1 | 12/2011 | Mahfouz |
| 2012/0178069 A1 | 7/2012 | McKenzie et al. |
| 2013/0041368 A1 | 2/2013 | Cunningham et al. |
| 2013/0237811 A1* | 9/2013 | Mihailescu ........... A61B 8/4245 600/407 |
| 2013/0307955 A1 | 11/2013 | Deitz et al. |
| 2013/0331859 A1 | 12/2013 | Kumar et al. |
| 2014/0005684 A1 | 1/2014 | Kim et al. |
| 2014/0039517 A1 | 2/2014 | Bowling et al. |
| 2014/0046128 A1 | 2/2014 | Lee et al. |
| 2014/0081659 A1 | 3/2014 | Nawana et al. |
| 2014/0107471 A1 | 4/2014 | Haider et al. |
| 2014/0199673 A1 | 7/2014 | Jian et al. |
| 2014/0200440 A1 | 7/2014 | Iannotti et al. |
| 2014/0228860 A1 | 8/2014 | Steines et al. |
| 2014/0272867 A1 | 9/2014 | Ratcliffe et al. |
| 2014/0276943 A1 | 9/2014 | Bowling et al. |
| 2014/0287393 A1 | 9/2014 | Kumar et al. |
| 2014/0343913 A1 | 11/2014 | Avisar |
| 2014/0379132 A1 | 12/2014 | Fudaba et al. |
| 2015/0298318 A1 | 10/2015 | Wang et al. |
| 2015/0356252 A1 | 12/2015 | Beker |
| 2016/0098933 A1 | 4/2016 | Reiley et al. |
| 2016/0106616 A1 | 4/2016 | Kim et al. |
| 2016/0157832 A1 | 6/2016 | Kang et al. |
| 2017/0367766 A1 | 12/2017 | Mahfouz |
| 2018/0153505 A1 | 6/2018 | Cadieu et al. |
| 2018/0153632 A1 | 6/2018 | Tokarchuk et al. |
| 2018/0345557 A1 | 12/2018 | Kang et al. |
| 2019/0029766 A1 | 1/2019 | Griffiths et al. |
| 2019/0090969 A1 | 3/2019 | Jarc et al. |
| 2021/0282804 A1 | 9/2021 | Worrell et al. |
| 2021/0315650 A1 | 10/2021 | Tokarchuk et al. |

FOREIGN PATENT DOCUMENTS

| | | | |
|---|---|---|---|
| CN | 101160104 B | 7/2012 | |
| CN | 103249368 A | 8/2013 | |
| CN | 103705306 A | 4/2014 | |
| CN | 103961178 A | 8/2014 | |
| CN | 104203078 A | 12/2014 | |
| CN | 104271046 A | 1/2015 | |
| CN | 104582624 A | 4/2015 | |
| CN | 104661612 A | 5/2015 | |
| EP | 1356781 A2 | 10/2003 | |
| EP | 1443416 A1 | 8/2004 | |
| JP | 2000287986 A | 10/2000 | |
| JP | 2003150569 A | 5/2003 | |
| JP | 2007534351 A | 11/2007 | |
| JP | 2012065698 A | 4/2012 | |
| JP | 2013543764 A | 12/2013 | |
| KR | 20150047478 A | 5/2015 | |
| WO | WO-2006091494 A1 | 8/2006 | |
| WO | WO-2010039394 A1 | 4/2010 | |
| WO | WO-2012065175 A2 | 5/2012 | |
| WO | WO-2012158324 A2 | 11/2012 | |
| WO | WO-2014005139 A2 | 1/2014 | |
| WO | WO-2014139021 A1 | 9/2014 | |
| WO | WO-2015066565 A1 | 5/2015 | |
| WO | WO-2015095715 A1 * | 6/2015 | ............ G09B 23/28 |
| WO | WO-2016201123 A1 | 12/2016 | |
| WO | WO-2017083768 A1 | 5/2017 | |

OTHER PUBLICATIONS

Extended European Search Report for Application No. 16808303.8, dated May 20, 2019, 14 pages.

Extended European Search Report for Application No. 16865162.8 dated Jul. 3, 2019, 11 pages.

International Preliminary Report on Patentability for Application No. PCT/US2016/036733, dated Dec. 21, 2017, 11 pages.

International Preliminary Report on Patentability for Application No. PCT/US2016/061694, dated May 24, 2018, 6 pages.

International Search Report and Written Opinion for Application No. PCT/US16/36733, dated Oct. 12, 2016, 15 pages.

International Search Report and Written Opinion for Application No. PCT/US2016/061694, dated Feb. 20, 2017, 10 pages.

Lalys F., et al., "A Framework for the Recognition of High-Level Surgical Tasks from Video Images for Cataract Surgeries," IEEE Transactions on Bio-medical Engineering, Apr. 2012, vol. 59 (4), pp. 966-976.

Office Action dated Apr. 27, 2020 for Chinese Application No. 201680038267 filed Jun. 9, 2016, 29 pages.

Partial Supplementary European Search Report for Application No. 16808303.8, dated Jan. 28, 2019, 16 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Voros S., et al., "Towards "Reaktime" Tool-tissue Interaction Detection in Robotically Assisted Laparoscopy," Proceedings of 2nd IEEE RAS & EMBS International Conference on Biomedical Robotics and Biomechatronics, Oct. 2008, pp. 562-567.

(56) References Cited

OTHER PUBLICATIONS

European Application for Serial No. EP16865162.8, Communication Pursuant to Article 94(3) EPC dated May 10, 2023, 09 pages.

* cited by examiner

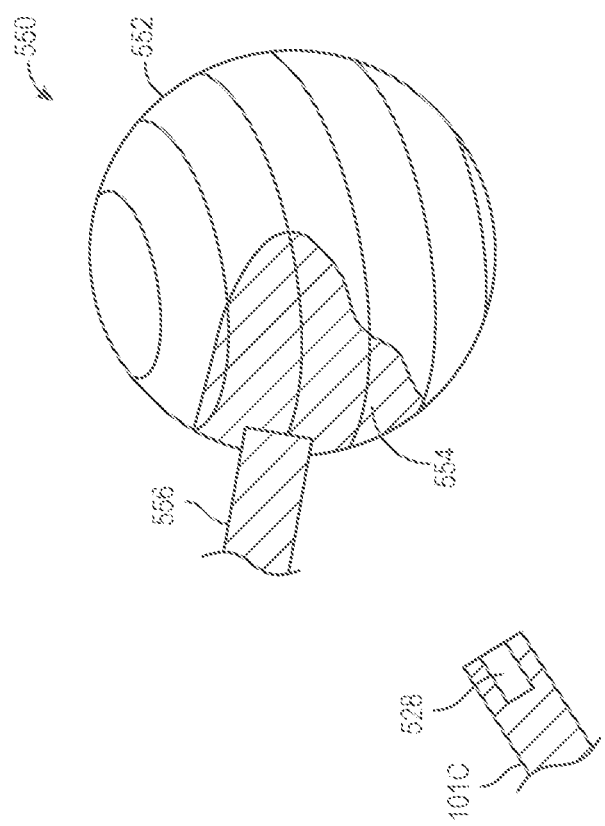
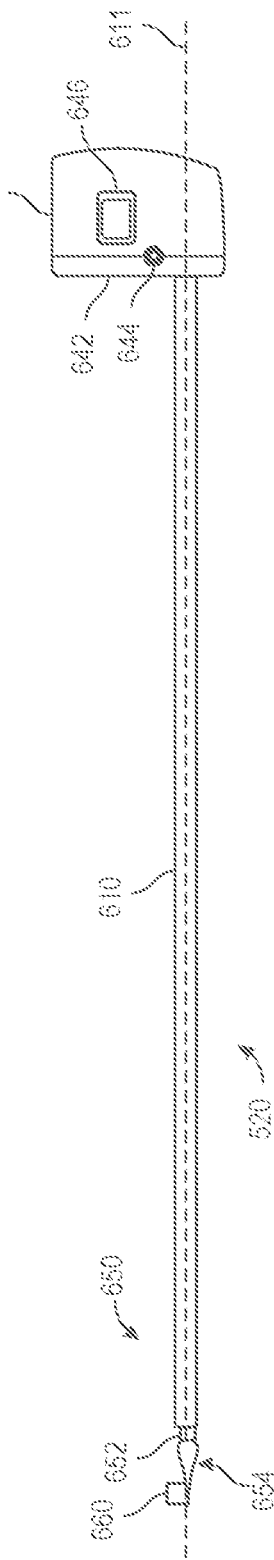
FIG. 5C
FIG. 6

SURGICAL SYSTEM WITH TRAINING OR ASSIST FUNCTIONS

CLAIM OF PRIORITY

This application is a continuation of and claims the benefit of priority under 35 U.S.C. § 120 to U.S. patent application Ser. No. 15/772,531, filed on Apr. 30, 2018, which is a U.S. National Stage Filing under 35 U.S.C. 371 from International Application No. PCT/US2016/061694, filed on Nov. 11, 2016, and published as WO 2017/083768 A1 on May 18, 2017, which claims the benefit of priority to U.S. Provisional Patent Application No. 62/374,670, filed on Aug. 12, 2016, and claims the benefit of priority to U.S. Provisional Patent Application No. 62/254,556, filed on Nov. 12, 2015, each of which is incorporated by reference herein in its entirety.

FIELD OF INVENTION

Inventive aspects are associated with medical devices used in connection with surgery. More specifically, aspects are associated with controlling a robot-assisted surgical system to gather and assess surgery-performance data to automatically assist or advise surgical personnel.

BACKGROUND

Minimally invasive teleoperated surgical systems (TSSs) have been developed to increase a surgeon's dexterity when working on an internal surgical site, as well as to allow a surgeon to operate on a patient from a remote location (outside the sterile field). In a TSS, the surgeon is often provided with an image of the surgical site at a control console. While viewing an image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the TSS can provide mechanical actuation and control of a variety of surgical instruments or tools having end effectors that perform various functions for the surgeon, for example, holding or driving a needle, grasping a blood vessel, dissecting tissue, stapling tissue, or the like, in response to manipulation of the master input devices.

It is desirable to train surgeons to use the TSS and to assist surgeons with surgeries using the TSS. Practical solutions are needed to facilitate automated surgical assessment and automated surgical assistance, where appropriate.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

One aspect of the invention is directed to a surgeon-support system for a teleoperated surgical system (TSS). The TSS generally includes a surgeon input interface that accepts surgical control input for effecting an electromechanical surgical system to carry out a surgical procedure.

In some embodiments, the surgeon-support system includes a virtual surgical environment engine, and an assist engine, each of which may be implemented using computing hardware.

The virtual surgical environment engine includes a surgical input assessor engine to receive surgical input including monitored events of the TSS, and a segmenter engine to determine a current stage of the surgical procedure based on the surgical input.

The assist engine includes a TSS interface communicatively coupled to the surgeon input interface of the TSS, an assistance call detector to detect a call for surgeon assistance, and an assistance rendering engine to send context-relevant assistance via the TSS interface in response to the call for surgeon assistance. The context-relevant assistance is stage-synchronized with the surgical procedure. Stage synchronization refers to alignment in terms of surgical process flow, rather than strict temporal alignment. In some embodiments, stage synchronization supports stage-offsetting such that assistance may be provided to prepare the surgeon or surgical team for an upcoming stage of the surgical procedure.

Advantageously, stage-synchronization provides the surgeon with context-relevant assistance, which may be made immediately available. Examples of assistance include automatically-queued expert video segments of current (or upcoming) portions of the surgical procedure, on-demand simulation of a current or upcoming portion of the surgical procedure, which may be called upon intra-operatively in some cases, scenario-specific surgical technique advice from an automated expert system, and notification of a human expert-assistant previously assessed to have expertise in the particular portion of the surgical procedure. The foregoing examples are provided for illustration, and are not to be considered scope-limiting unless, and to the extent, they are expressly called out in the appended claims.

In some embodiments, the virtual surgical environment engine is further configured to implement a simulator engine to process a computational model of a surgical procedure based on the surgical input of the TSS. For example, the simulator engine may include a TSS model to computationally represent the TSS in the virtual surgical environment; and a patient model to computationally represent the patient based on the patient's physical characteristics, and changes to the patient effected by operation of the TSS model.

In some embodiments, the surgeon-support system includes a surgical technique assessor engine configured to access the surgical input and the current stage of the surgical procedure, and compute a plurality of temporal and spatial metrics of the surgical input corresponding to a plurality of different stage of the surgical procedure including the current stage. The surgical technique assessor engine may generate a surgical stage-specific performance score representing a quality of surgical performance of a surgeon producing the surgical control input.

BRIEF DESCRIPTION OF THE DRAWINGS

FIG. 5C is an illustrative view of a surgical scene.

FIG. 6 is an elevation view of a surgical instrument.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the scope of this description and the claims. In some instances, well-known circuits, structures, or techniques have not been shown or described in detail in order not to obscure the invention. Like numbers in two or more figures represent the same or similar elements.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® Surgical System (specifically, a Model IS4000, marketed as the da Vinci Xi® Surgical System), commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the da Vinci Xi® Surgical System, the da Vinci Si® Surgical System) are merely illustrative, and are not to be considered as limiting the scope of the inventive aspects disclosed herein to any particular model or apparatus, unless, and to the extent that those limitations are expressly called out in one or more claims.

Minimally Invasive Teleoperated Surgical System (TSS)

Teleoperation refers to operation of a machine at a distance. In a minimally invasive teleoperation medical system, a surgeon may use an endoscope that includes a camera to view a surgical site within a patient's body. In some embodiments, stereoscopic images can be captured, which allow the perception of depth during a surgical procedure.

Figure 1:
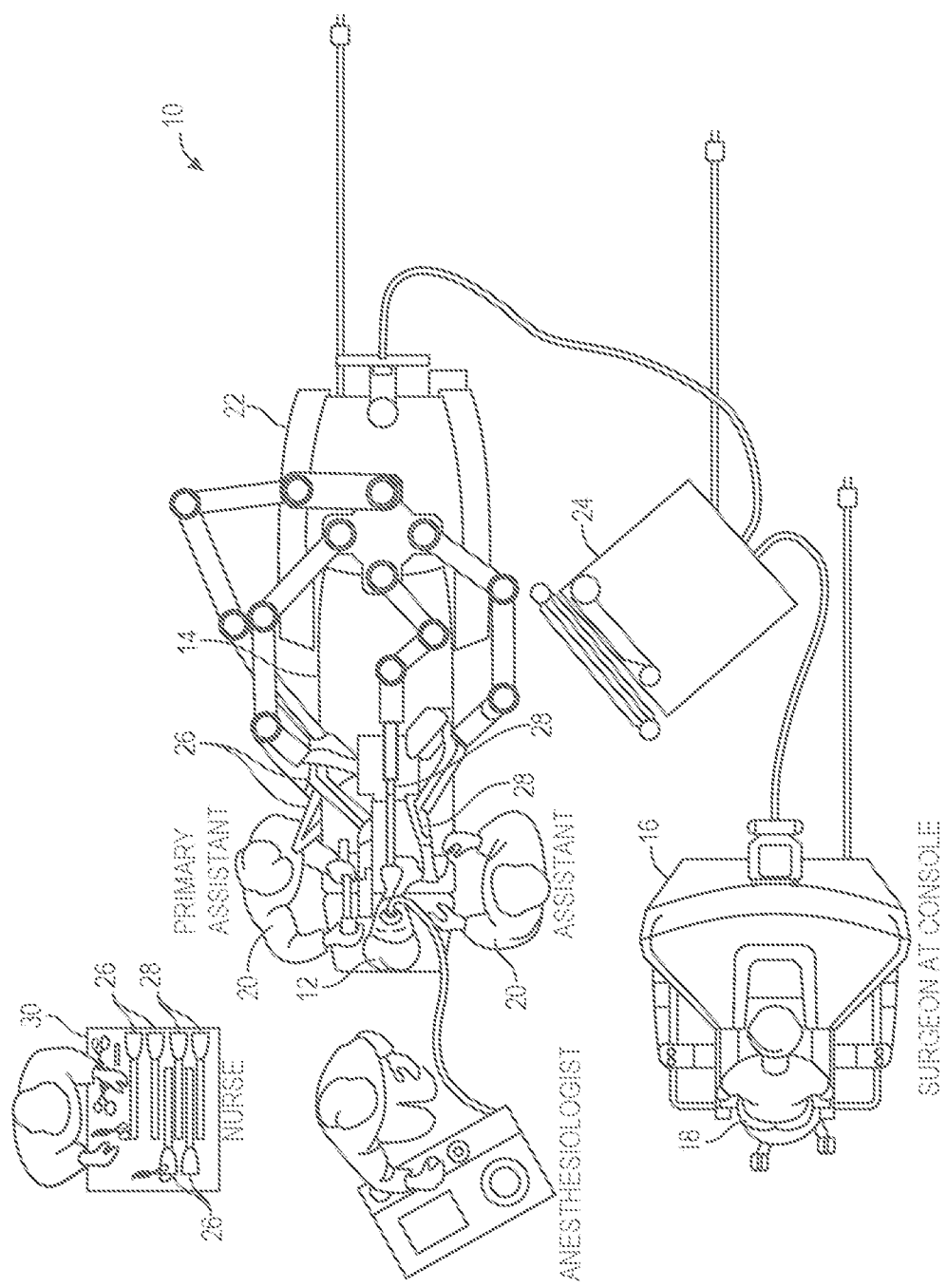
FIG. 1 is a plan view of a minimally invasive teleoperated surgical system (TSS).

Referring now to the drawings, in which like reference numerals represent like parts throughout the several views, FIG. 1 is a plan view of a minimally invasive TSS 10, typically used for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive TSS 10 further includes a patient-side cart(s) 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by a camera mounted with an endoscope 28, such as a stereoscopic endoscope, which can be manipulated by the patient-side cart 22 to position and orient the endoscope 28. Computer processors located on the electronics cart 24 can be used to process the images of the surgical site for subsequent display to the surgeon 18 through the surgeon's console 16. Note that while discrete system components (i.e., patient side cart 22, electronics cart 24, and surgeon's console 16) are depicted and described for exemplary purposes, in various embodiments the elements included therein can be combined and/or separated. For example, in some embodiments, the computer processors of electronics cart 24 can be incorporated into surgeon's console 16 and/or patient side cart 22. The number of surgical instruments 26 used at one time will generally depend on the diagnostic or surgical procedure and the space constraints within the operative site among other factors. If it is necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
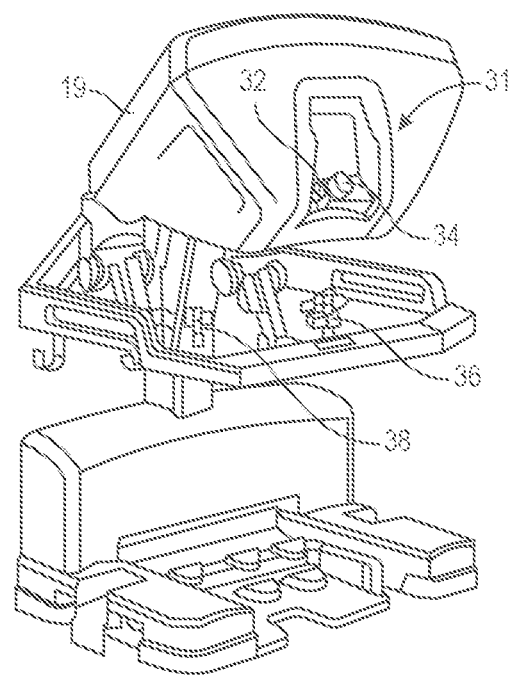
FIG. 2 is a perspective view of a surgeon's console.

FIG. 2 is a perspective view of the surgeon's console 16. The surgeon's console 16 includes a viewer 31 that includes a left eye display screen 32 and a right eye display screen 34 for presenting the surgeon 18 with a coordinated stereoscopic view of the surgical site that enables depth perception. In various other embodiments, a non-stereoscopic display can be provided for surgeon 18. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same or greater mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, in some embodiments, position, force, and tactile feedback sensors (not shown) may be employed to transmit position, force, and tactile sensations from the surgical instruments 26 back to the surgeon's hands through the control inputs 36, subject to communication delay constraints. Note that while a physical console 16 with a fixed viewer 31 and mechanically coupled control inputs 36 is depicted and described for exemplary purposes, in various other embodiments, "ungrounded" control inputs and/or display structures can be used. For example, in some embodiments, viewer 31 can be a head-mounted display and/or control inputs 36 can be mechanically independent of any base structure (e.g., wired, wireless, or gesture-based, such as Kinect from Microsoft).

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
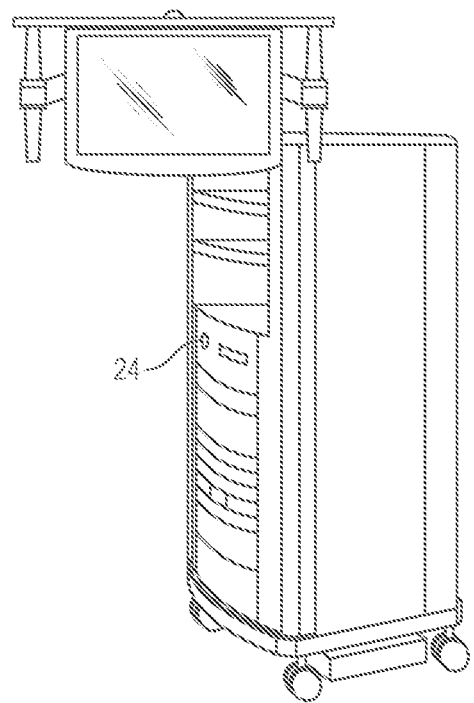
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
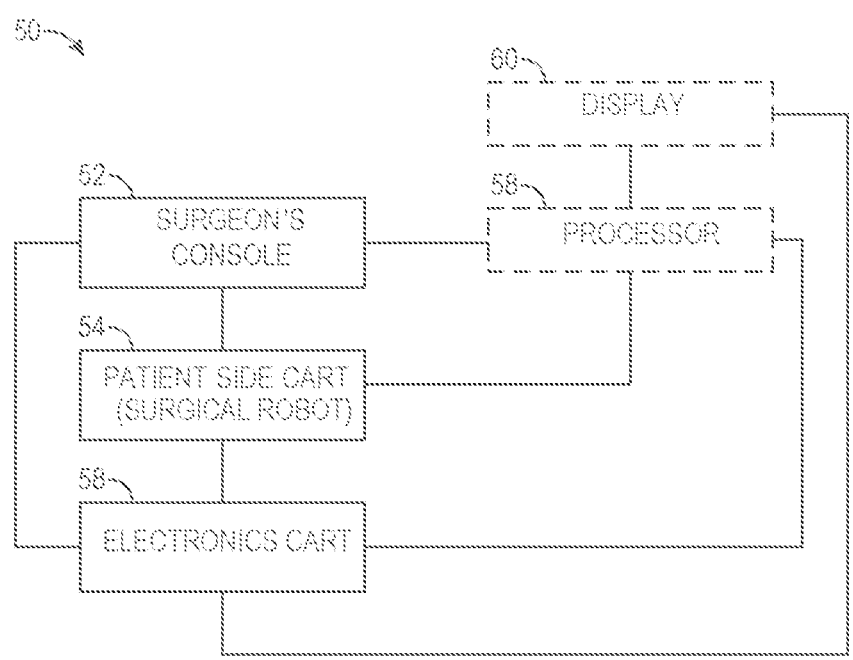
FIG. 4 is a diagrammatic illustration of a TSS.

FIG. 4 diagrammatically illustrates a TSS 50 (such as the minimally invasive TSS 10 of FIG. 1). A surgeon's console 52 (such as surgeon's console 16 in FIG. 1) can be used by a surgeon to control a patient-side cart 54 (such as patent-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Additionally or in the alternative, the captured images can undergo image processing by a computer processor located outside of electronics cart 56. In one aspect, TSS 50 includes an optional computer processor 58 (as indicated by dashed line) similar to the computer processor located on electronics cart 56, and patient-side cart 54 outputs the captured images to computer processor 58 for image processing prior to display on the surgeon's console 52. In another aspect, captured images first undergo image processing by the computer processor on electronics cart 56 and then undergo additional image processing by computer processor 58 prior to display on the surgeon's console 52. TSS 50 can include an optional display 60, as indicated by dashed line. Display 60 is coupled with the computer processor located on the electronics cart 56 and with computer processor 58, and captured images processed by these computer processors can be displayed on display 60 in addition to being displayed on a display of the surgeon's console 52.

Figure 5A:
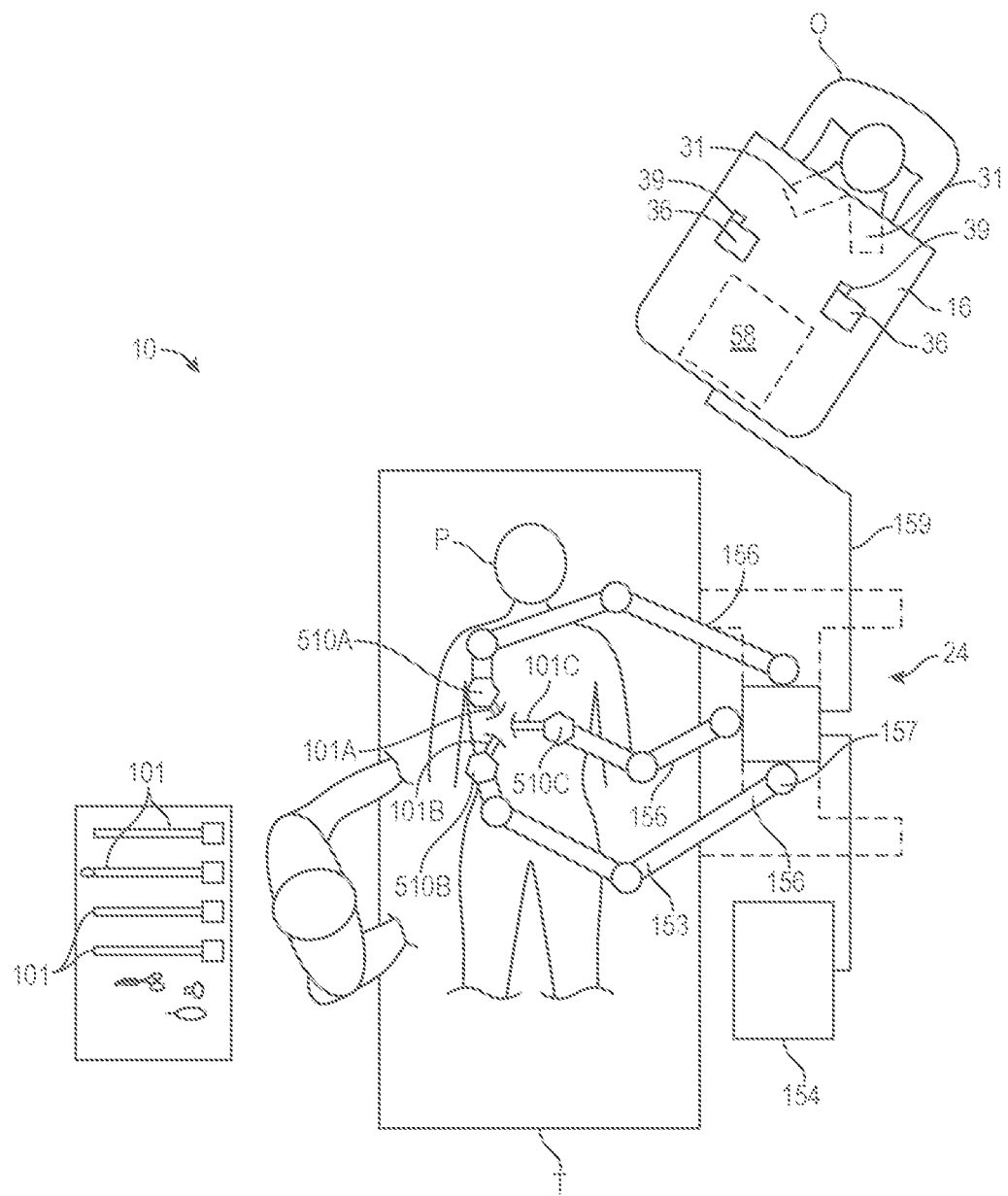
FIG. 5A is an illustrative diagram of the TSS.

FIG. 5A is an illustrative simplified block diagram showing arrangement of components of the teleoperation surgery system 10 to perform surgical procedures using one or more mechanical support arms 510 in accordance with some embodiments. Aspects of system 10 includes robot-assisted and autonomously operating features. These mechanical support arms 510 often support a surgical instrument. For instance, a mechanical surgical arm (e.g., the center mechanical surgical arm 510C) may be used to support an endoscope with a stereo or three-dimensional surgical image capture device 101C. The mechanical surgical arm 510C may include a sterile adapter, or a clamp, clip, screw, slot/groove, or other fastener mechanism to mechanically secure an endoscope that includes the image capture device 101C to the mechanical arm. In various other embodiments, image capture device 101C (or any other surgical instrument) can be integrated into mechanical surgical arm 510C.

A user or operator O (generally a surgeon) performs a surgical procedure on patient P by manipulating control input devices 36, such as hand grips and foot pedals at a master control console 16. The operator can view video frames of images of a surgical site inside a patient's body through a stereo display viewer 31. A computer processor 58 of the console 16 directs movement of teleoperationally controlled endoscopic surgical instruments 101A-101C via control lines 159, effecting movement of the instruments using a patient-side system 24 (also referred to as a patient-side cart).

The patient-side system 24 includes one or more mechanical support arms 510. Typically, the patient-side system 24 includes at least three mechanical surgical arms 510A-510C (generally referred to as mechanical surgical support arms 510) supported by corresponding positioning set-up arms 156. The central mechanical surgical arm 510C may support or include an endoscopic camera 101C suitable for capture of images within a field of view of the camera. The mechanical surgical support arms 510A and 510B to the left and right of center may support or include instruments 101A and 101B, respectively, which may manipulate tissue.

Figure 5B:
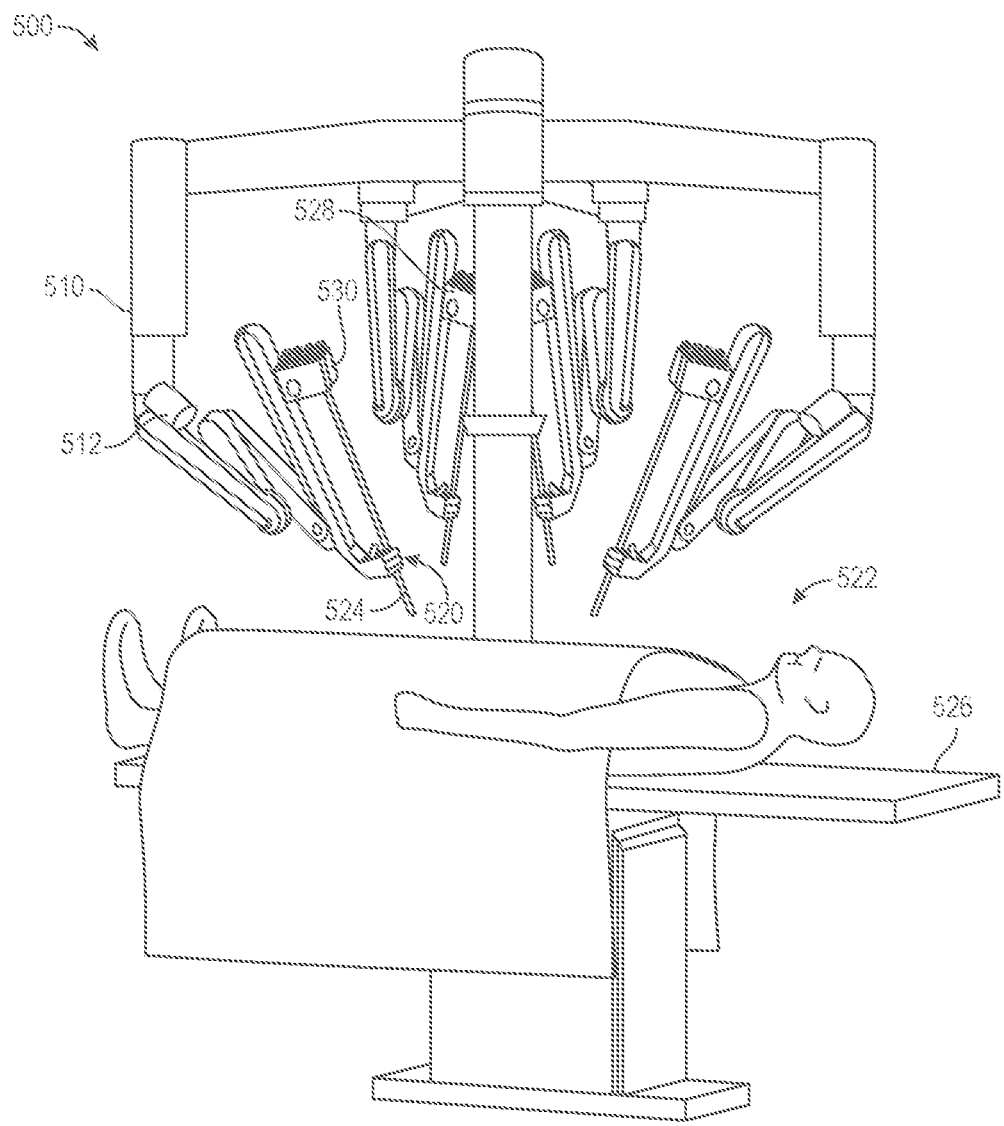
FIG. 5B is a perspective view of a patient-side cart of the surgical system.

FIG. 5B is a perspective view of a patient-side cart 500 of a minimally invasive TSS 10, in accordance with embodiments. The patient-side cart 500 includes one or more support arm assemblies 510. A surgical instrument manipulator 512 is mounted at the end of each support arm assembly 510. Additionally, each support arm assembly 510 can optionally include one or more setup joints (e.g., unpowered and/or lockable) that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while a single patient-side cart 500 is shown as including four surgical instrument manipulators 512, multiple patient side carts 500 and/or more or fewer surgical instrument manipulators 512 on patient side cart(s) 500 can be provided.

A functional TSS will generally include a vision system portion that enables a user of the TSS to view the surgical site from outside the patient's body 522. The vision system typically includes a camera instrument 528 for capturing video images and one or more video displays for displaying the captured video images. In some surgical system configurations, the camera instrument 528 includes optics that transfer the images from a distal end of the camera instrument 528 to one or more imaging sensors (e.g., CCD or CMOS sensors) outside of the patient's body 522. Alternatively, the imaging sensor(s) can be positioned at the distal end of the camera instrument 528, and the signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, Calif.

Referring to FIGS. 5A-5B, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

In one aspect, surgical instruments 520 are controlled through computer-assisted teleoperation. A functional minimally invasive TSS includes a control input that receives inputs from a user of the TSS (e.g., a surgeon or other medical person). The control input is in communication with one or more computer-controlled teleoperated actuators, such as one or more motors to which surgical instrument 520 is coupled. In this manner, the surgical instrument 520 moves in response to a medical person's movements of the control input. In one aspect, one or more control inputs are included in a surgeon's console such as surgeon's console 16 shown at FIG. 2. A surgeon can manipulate control input devices 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIGS. 5A-5B, in one aspect, a surgical instrument 520 and a cannula 524 are removably coupled to manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. In one aspect, the instrument carriage 530 houses one or more teleoperated actuators inside that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In accordance with some embodiments, the surgical system 10 can have multiple system actuation states including docked, following, instrument types, head-in, camera movement, third arm control, ergonomic adjustments, table motion adjustment, etc. During a docked system state, one or more manipulator 512 have been coupled to cannula 524. During a following system state, the surgical instrument ("slave") is tracking the control input ("master" command). During an instrument-types system state, the system has installed in it a set of instruments suitable for performance of a particular surgical procedure or suitable for performance of a particular surgical activity during a surgical procedure. During a head-in system state, the system is waiting for the surgeon to indicate he/she has taken hold of the "master" control input device.

In an alternate embodiment, instrument carriage 530 does not house teleoperated actuators. Teleoperated actuators that enable the variety of movements of the end effector of the surgical instrument 520 are housed in a location remote from the instrument carriage 530, e.g., elsewhere on patient-side cart 500. A cable-based force transmission mechanism or the like is used to transfer the motions of each of the remotely located teleoperated actuators to a corresponding instrument-interfacing actuator output located on instrument carriage 530. In some embodiments, the surgical instrument 520 is mechanically coupled to a first actuator, which controls a first motion of the surgical instrument such as longitudinal (z-axis) rotation. The surgical instrument 520 is mechanically coupled to a second actuator, which controls second motion of the surgical instrument such as two-dimensional (x, y) motion. The surgical instrument 520 is mechanically coupled to a third actuator, which controls third motion of the surgical instrument such as opening and closing or a jaws end effector.

FIG. 5C is an illustrative view representing a surgical scene 550 and also showing an endoscope 101C mounting a camera 528 used to record the scene in accordance with some embodiments. The scene 550 is disposed within a patient's body cavity. The scene 550 includes an example hypothetical spherical anatomical structure 552 that includes geometric contours 554. The scene 550 encompasses a surgical instrument 556. A camera 528 mounted on an endoscope 101C captures the scene, which is displayed within the viewer 31 and which is recorded for playback later.

FIG. 6 is a side view of a surgical instrument 520, which includes a distal portion 650 and a proximal control mechanism 640 coupled by an elongate tube 610 having an elongate tube centerline axis 611. The surgical instrument 520 is configured to be inserted into a patient's body and is used to carry out surgical or diagnostic procedures. The distal portion 650 of the surgical instrument 520 can provide any of a variety of end effectors 654, such as the forceps shown, a needle driver, a cautery device, a cutting tool, an imaging device (e.g., an endoscope or ultrasound probe), or the like. The surgical end effector 654 can include a functional mechanical degree of freedom, such as jaws that open or close, or a knife that translates along a path. In the embodiment shown, the end effector 654 is coupled to the elongate tube 610 by a wrist 652 that allows the end effector to be oriented relative to the elongate tube centerline axis 611. Surgical instrument 520 can also contain stored (e.g., on a semiconductor memory associated with the instrument) information, which may be permanent or may be updatable by a surgical system configured to operate the surgical instrument 520. Accordingly, the surgical system may provide for either one-way or two-way information communication between the surgical instrument 520 and one or more components of the surgical system.

Figure 7:
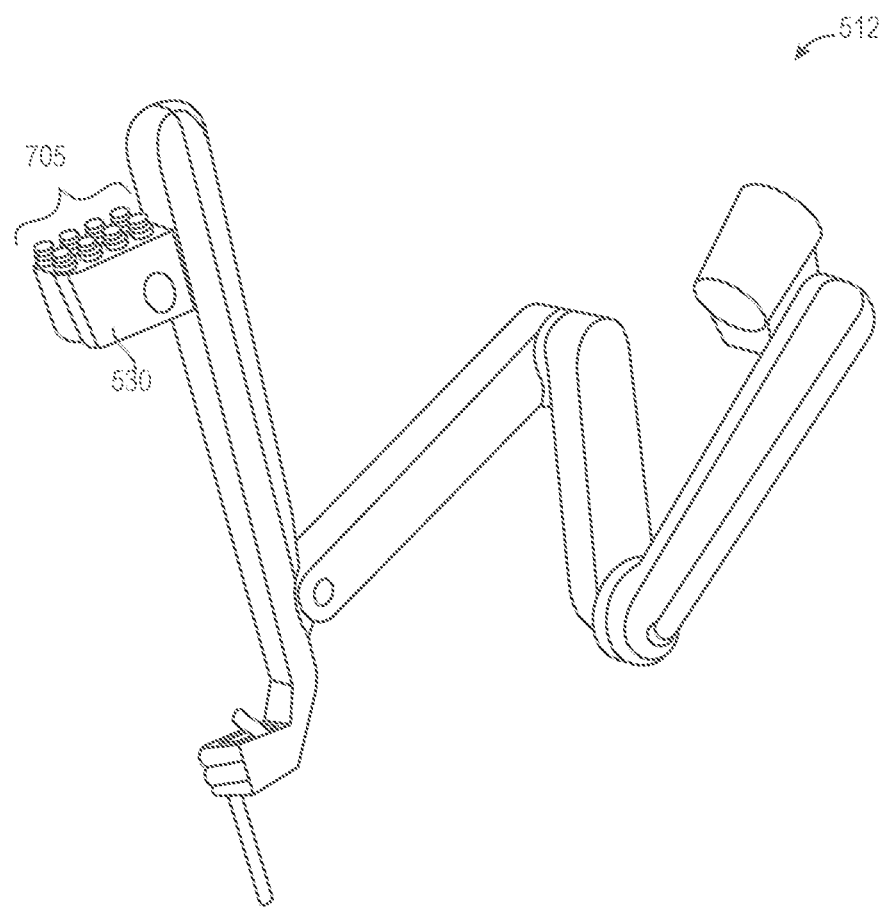
FIG. 7 is a perspective view of an instrument manipulator.

FIG. 7 is a perspective view of surgical instrument manipulator 512. Instrument manipulator 512 is shown with no surgical instrument installed. Instrument manipulator 512 includes an instrument carriage 530 to which a surgical instrument (e.g., surgical instrument 520) can be detachably connected. Instrument carriage 530 houses a plurality of teleoperated actuators. Each teleoperated actuator includes an actuator output 705. When a surgical instrument is installed onto instrument manipulator 512, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs 705 directly contacting corresponding instrument inputs. In another aspect, this mechanical coupling occurs through an intermediate interface, such as a component of a drape configured to provide a sterile barrier between the instrument manipulator 512 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 512 is surgical instrument 520, shown at FIG. 6. Referring to FIG. 6, in one aspect, movement of one or more instrument inputs of proximal control mechanism 640 by corresponding teleoperated actuators rotates elongate tube 610 (and the attached wrist 652 and end effector 654) relative to the proximal control mechanism 640 about elongate tube centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.). Accordingly, various mechanical degrees of freedom of a surgical instrument installed onto an instrument manipulator 512 can be moved by operation of the teleoperated actuators of instrument carriage 530.

Surgical Planning System

Figure 8:
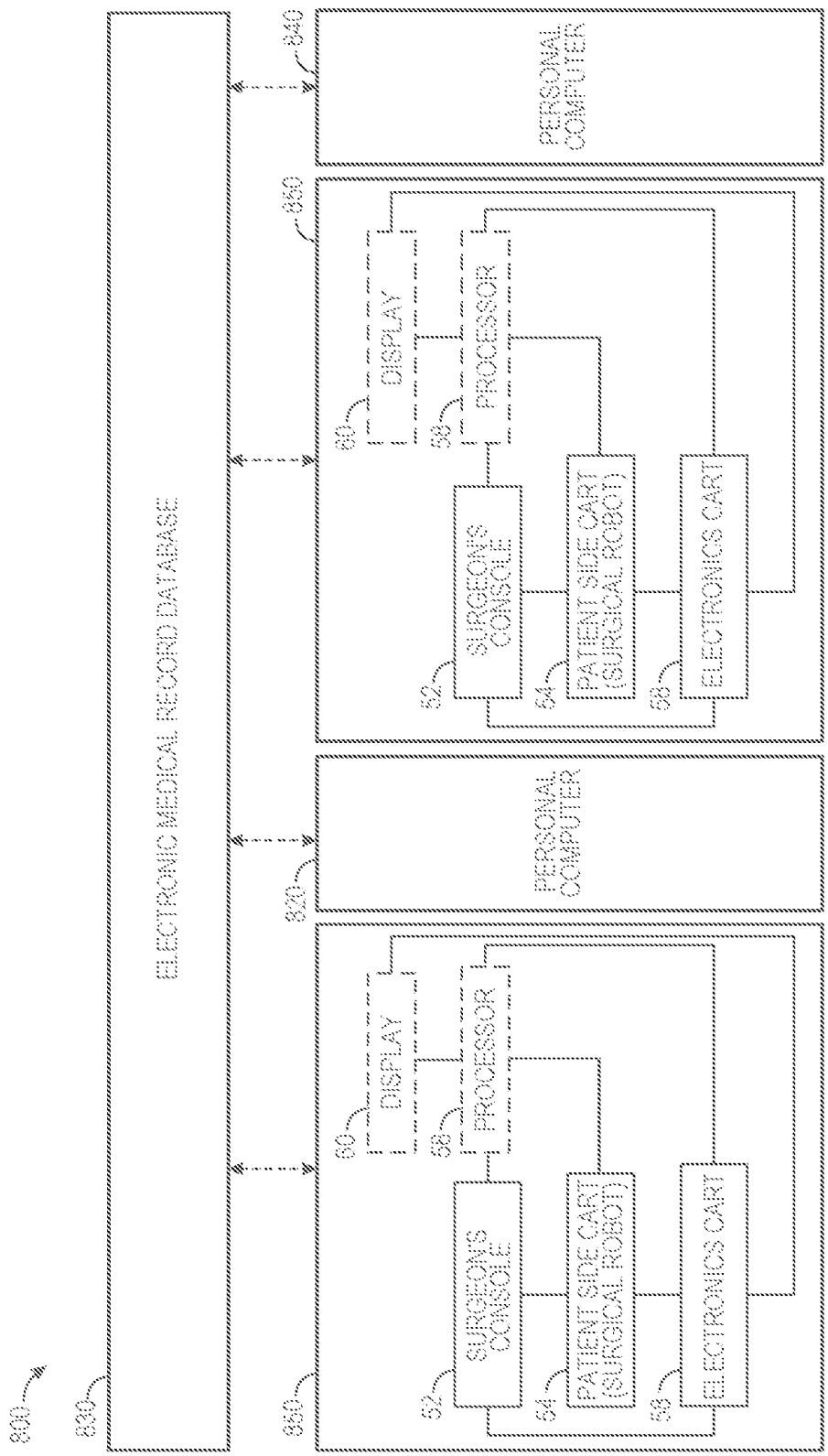
FIG. 8 is a diagrammatic illustration of a surgical planning tool.

FIG. 8 shows a schematic diagram of an exemplary surgical planning tool 800. In one aspect, surgical planning tool 800 includes a TSS 850 in data communication with an electronic medical device record database 830. TSS 850 shown here is similar to TSS 50 shown at FIG. 4. In one aspect, electronic medical record database 830 includes the medical records of patients that have undergone treatment at a particular hospital or at a plurality of hospitals. Database 830 can be implemented on a server located on-site at the hospital. The medical record entries contained in the database 830 can be accessed from hospital computers through an intranet network. Alternatively, database 830 can be implemented on a remote server located off-site from the hospital, e.g., using one of a number of cloud data storage services. In this case, medical record entries of database 830 are stored on the cloud server, and can be accessed by a computer system with Internet access.

In one aspect, a surgical procedure is performed on a first patient using TSS 850. An imaging device associated with TSS 850 captures images of the surgical site and displays the captured images as frames of a video on a display of surgeon's console 52. In one aspect, a medical person at surgeon's console 52 highlights or annotates certain patient anatomy shown in the displayed video using an input device of surgeon's console 52. An example of such an input device is left and right handgrip control inputs 36, 38, respectively, shown at FIG. 2, which is coupled to a cursor that operates in conjunction with a graphic user interface overlaid onto the displayed video. The graphic user interface can include a QWERTY keyboard, a pointing device such as a mouse and an interactive screen display, a touch-screen display, or other means for data or text entry or voice annotation/or speech to text conversion via a microphone and processor. Accordingly, the medical person can highlight certain tissue of interest in the displayed image or enter a text annotation.

In one aspect, the surgical site video is additionally displayed on a display located on electronics cart 56. In one aspect, the display of electronics cart is a touch-screen user interface usable by a medical person to highlight and annotate certain portions of patient anatomy shown on an image that is displayed for viewing on the display on the electronics cart. A user, by touching portions of patient anatomy displayed on the touch-screen user interface, can highlight portions of the displayed image. Additionally, a graphic interface including a keyboard can be overlaid on the displayed image. A user can use the keyboard, or other input device, such as a microphone and a speech-to-text conversion driver to enter text annotations.

In one aspect, the surgical site video captured by the imaging device associated with TSS 850 is recorded by the TSS 850, and stored in database 830, in addition to being displayed in real time or near real time to a user. Highlights and/or annotations associated with the recorded video that were made by the user can also be stored on database 830. In one aspect, the highlights made by the user are embedded with the recorded video prior to its storage on database 830. At a later time, the recorded video can be retrieved for viewing. In one aspect, a person viewing the recorded video can select whether the highlights are displayed or suppressed from view. Similarly, annotations associated with the recorded video can also be stored on database 830. In one aspect, the annotations made by the user are used to tag the recorded video, and can be used to provide as a means of identifying the subject matter contained in the recorded video. For example, one annotation may describe conditions of a certain disease state. This annotation is used to tag the recorded video. At a later time, a person desiring to view recorded procedures concerning this disease state can locate the video using a key word search.

Retrieval of Stored Video

In some cases, it is desirable for a medical person to be able to view video recordings of past surgical procedures performed on a given patient. In one aspect, a patient who previously underwent a first surgical procedure to treat a medical condition subsequently requires a second surgical procedure to treat recurrence of the same medical condition or to treat anatomy located nearby to the surgical site of the first surgical procedure. In one aspect, the surgical site events of the first surgical procedure were captured in a surgical site video recording, and the video recording was archived in database 830 as part of the patient's electronic medical records. In a related embodiment, the first surgical procedure may be indexed according to type of procedure. Prior to performing the second surgical procedure on the patient, a medical person can perform a search of database 830 to locate the video recording of the patient's earlier surgical procedure.

In some cases, it is desirable for a medical person planning to perform a surgical procedure on a patient to be able to view video recordings of similar surgical procedures performed on persons having certain characteristics similar to the patient. In one aspect, surgical site video recordings of surgical procedures can be tagged with metadata information such as the patient's age, gender, body mass index, genetic information, type of procedure the patient underwent, etc., before each video recording is archived in database 830. In one aspect, the metadata information used to tag a video recording is automatically retrieved from a patient's then-existing medical records, and then used to tag the video recording before the video recording is archived in database 830. Accordingly, prior to performing a medical procedure on a patient, a medical person can search database 830 for video recordings of similar procedures performed on patients sharing certain characteristics in common with the patient. For example, if the medical person is planning to use TSS 850 to perform a prostatectomy on a 65 year-old male patient with an elevated body mass index, the medical person can search database 830 for surgical site video recordings of prostatectomies performed using TSS 850 on other males of similar age and having similarly elevated body mass index.

In one aspect, a video recording of a surgical procedure is communicated by database 830 to an optional personal computing device 820 (as indicated by dashed line), such as a personal computer, tablet, smartphone, terminal, or other electronic access device, and made available for viewing by a medical person who plans to perform a surgical procedure. Additionally or in the alternative, the video recording of the earlier surgical procedure can be communicated by database 830 to TSS 850, and made available for viewing preoperatively or intraoperatively. In one aspect, the video recording is displayed by TSS 850 on a display located on surgeon's console 52. In another aspect, the video recording of the first surgical procedure is displayed on a display located on electronics cart 56.

In a related embodiment, as described in greater detail below, the video recording of the earlier procedure may be stage-synchronized, or stage-queueable with the current surgical procedure, facilitating immediate locating of relevant surgical tasks or techniques, such as those to be used in an upcoming stage of the current procedure. Queuing the video playback to the present stage of the surgical procedure allows the surgeon to very efficiently scroll the playback to see upcoming or recent steps. Notably, stage-synchronization or stage-queueability is not strictly time-synchronized, though there is a general time-ordering similarity between the previous and the current surgical procedures. Rather, as discussed above, the stage synchronization is aligned in terms of surgical process flow. Matching of direct visual features through video matching can be enhanced through one of more of (a) meta-data, (b) stage-synchronization, and (c) temporal synchronization.

Alternatively, video sequences from a current surgery can be matched to video sequences from a representative surgery performed by a skilled surgeon by matching, based on visual similarity (e.g., colors, time, edges, etc.) or content similarity (e.g., organs, anatomy, tools, etc.) if content can be recognized using computer vision methods.

Cloud-Based Video Database

In one aspect, database 830 is implemented on a remote server using a cloud data storage service and is accessible by multiple health care providers. Referring to FIG. 8, as shown by dashed line, surgical planning tool 800 optionally includes TSS 850 (as indicated by dashed line) and personal computing device 840 (as indicated by dashed line). In one aspect, TSS 850 is similar to TSS 850 and personal computing device 840 is similar to personal computing device 820, except that TSS 850 and personal computing device 820 are located at a first health care provider and TSS 850 and personal computing device 840 are located at a second location or even with a second health care provider. In one aspect, a first patient requires surgical treatment of a medical condition, and undergoes a surgical procedure using TSS 850 at the first health care provider. A video recording of the surgical procedure is archived on database 830. At a later time, a second patient requires surgical treatment of the same medical condition, and plans to receive surgical treatment using TSS 850 at the second health care provider. Prior to performing the surgical procedure on the second patient, a medical person accesses database 830 through a secure internet connection and searches database 830 for surgical site video recordings of similar procedures. In one aspect, the medical person treating the second patient is able to retrieve from database 830 the video recording of first patient's surgical procedure, without acquiring knowledge of the identity of the first patient. In this manner, the privacy of the first patient is maintained. In one aspect, the video recording of the first patient's surgical procedure includes highlights and/or annotations made by the medical person who treated the first patient.

Computer Based Pattern Matching and Analysis

Surgical planning tool 800 can includes a pattern matching and analysis algorithm implemented in the form of computer executable code. In one aspect, the pattern matching and analysis algorithm is stored in a non-volatile memory device of surgical planning tool 80, and is configured to analyze the video recordings archived in database 830. As discussed previously, each of the video recordings archived in database 830 can be tagged and/or embedded with certain metadata information. This metadata information can include patient information such as patient age, gender, and other information describing the patient's health or medical history. Additionally, as discussed previously, the metadata information can include highlights or annotations made by a medical person. In one aspect, these highlights and annotations are embedded with the video recording and archived together with the video in database 830.

In one aspect, pattern matching and analysis algorithm includes an image analysis component that identifies patterns in shapes and colors that are shared amongst multiple video recordings stored on database 830. The pattern matching and analysis algorithm then reviews the tagged metadata associated with this subset of video recordings to determine whether any words or phrases are frequently associated with videos within this subset. Metadata can be tagged through annotating text, translating audio to text, for example. These analyses performed by pattern matching and analysis algorithm can be used to assist medical persons in making determinations about patient anatomy, preferred surgical approaches, disease states, potential complications, etc.

Virtual Surgical Environment, Data Logging, and Surgeon Assessor

The TSS can record video of surgical procedures being carried out, along with the surgeon's inputs via the control console. In general, it is desirable to train and assist surgeons using such gathered data. However, system designers face numerous challenges in managing the massive quantity of collected data, extracting relevant portions of the data, and providing useful and unobtrusive assistance that would be welcomed by surgeons.

Figure 9:
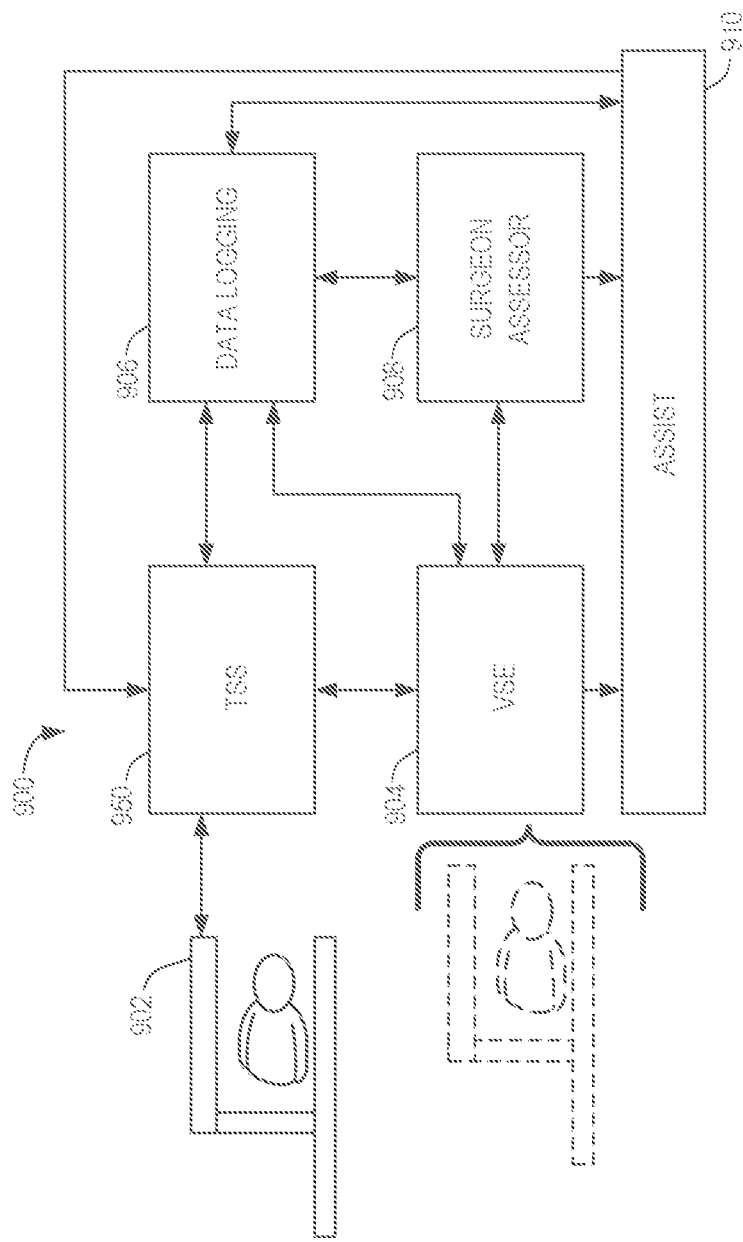
FIG. 9 is a diagram illustrating an advanced surgical system that features a TSS with additional support systems including a virtual surgical environment, a data logging system, a surgeon assessing system, and an assist system, according to various embodiments.

In various embodiments, as detailed below, a TSS is augmented, or supported, with additional special-purpose machinery to provide assessment, and assistance, for the medical personnel operating the TSS. FIG. 9 is a diagram illustrating an advanced surgical system 900 that features TSS 950, which is similar to TSS 50 described above in connection with FIG. 4, except that TSS 950 includes suitable interfaces to additional support systems, that include virtual surgical environment (VSE) 904, data logging system 906, surgeon assessor 908, and assist system 910. These additional support systems may each be realized in a variety of machine configurations. For instance, one or more of the additional systems may be provided as a dedicated unit, or as part of a computing platform through the execution of program instructions. The computing platform may be one physical machine, or may be distributed among multiple physical machines, such as by role or function, or by process thread in the case of a cloud computing distributed model. The computing platform may be implemented as part of TSS 950 in some embodiments (e.g., in surgeon's console 52, electronics cart 58, etc.), or it may be implemented using distinct hardware from the TSS (e.g., a mobile computing device such as a tablet, personal computer or laptop computer, smartphone, or some combination thereof). The computing platform can be implemented as a combination of local processing on system or personal hardware and the 'cloud'.

In various embodiments certain operations may run in virtual machines that in turn are executed on one or more physical machines. It will be understood by persons of skill in the art that features of the embodiments may be realized by a variety of different suitable machine implementations.

In various embodiments, these components are implemented as engines, circuits, components, or modules, which for the sake of consistency are termed engines, although it will be understood that these terms may be used interchangeably. Engines may be hardware, software, or firmware communicatively coupled to one or more processors in order to carry out the operations described herein. Engines may be hardware engines, and as such engines may be considered tangible entities capable of performing specified operations and may be configured or arranged in a certain manner. In an example, circuits may be arranged (e.g., internally or with respect to external entities such as other circuits) in a specified manner as an engine. In an example, the whole or part of one or more hardware processors may be configured by firmware or software (e.g., instructions, an application portion, or an application) as an engine that operates to perform specified operations. In an example, the software may reside on a machine-readable medium. In an example, the software, when executed by the underlying hardware of the engine, causes the hardware to perform the specified operations. Accordingly, the term hardware engine is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein.

Considering examples in which engines are temporarily configured, each of the engines need not be instantiated at any one moment in time. For example, where the engines comprise a general-purpose hardware processor core configured using software; the general-purpose hardware processor core may be configured as respective different engines at different times. Software may accordingly configure a hardware processor core, for example, to constitute a particular engine at one instance of time and to constitute a different engine at a different instance of time.

TSS 950 interfaces with surgical environment 902, in which the patient and medical personnel are facilitated. Generally speaking, the control inputs of TSS 950 are fed to electromechanical systems that cause a real-world effect in surgical environment 902. VSE 904, on the other hand, computationally models one or more portions of an actual surgical environment to create a virtual surgical environment according to some embodiments. Accordingly, the same control inputs of TSS 950 may be fed to VSE 904, where they produce a computationally-modeled effect in the virtual surgical environment.

In one type of embodiment, the virtual surgical environment includes a model of at least a portion of the patient, including physiologic structures, fluids, disease states, hemodynamics, or the like, in addition to the effects on the patient model of modeled electromechanical outputs representing the output of TSS 950. In another type of embodiment, the patient is not modeled; rather, the electromechanical outputs of TSS 950 are represented. In another type of embodiment, the control signaling that would be fed to the electromechanical systems of TSS 950 are modeled by VSE 904.

In a related embodiment, the virtual surgical environment 904 is programmed, or otherwise configured, to determine the stage, or segment, of a surgical procedure based on an assessment of surgical inputs that it receives from TSS 950.

In another related embodiment, VSE 904 is programmed, or otherwise configured, to determine the stage, or segment, of a surgical procedure based on the VSE-simulated effects of surgical inputs to the TSS, including effects in the simulated patient (e.g., effects in the tissue at the surgical site, hemodynamics, etc.), or other simulated features of the interaction of the patient with the surgical instruments, rather than the surgical inputs themselves. In another related embodiment, a combination of surgical inputs, and simulated effects thereof, are used in assessment of the segment of the surgical procedure.

Figure 10:
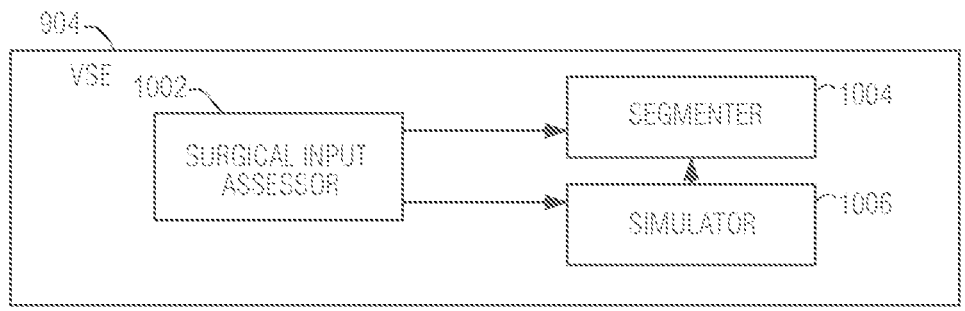
FIG. 10 is a diagram illustrating operational components, and their interactions, of a virtual surgical environment of the system of FIG. 9, according to an embodiment.

FIG. 10 is a diagram illustrating operational components, and their interactions, of VSE 904 according to an embodiment. Surgical input assessor 1002 is programmed, or otherwise configured, to gather event data, such as control inputs, kinematic information, sensor data, system events or status indications, among others, from TSS 950 and to interpret their meaning in terms of surgical effect. Segmenter 1004 is programmed, or otherwise configured, to discern the stages of surgical procedures as they are being performed, or in a post-processing mode. Simulator 1006 is programmed, or otherwise configured, to model a surgical procedure in the virtual surgical environment, based on the control inputs from TSS 950. Simulator 106 may operate in parallel with, or instead of, an actual surgical procedure being carried out in the surgical environment 902, and may be used by a surgeon to practice certain procedures or portions thereof. In some embodiments, simulator 1006 may be called upon during a specific portion of a procedure to allow the surgeon to practice a certain task before actually carrying out the task on a patient. More generally, simulator 1006 may be used for training and practice by surgeons, students, or other medical personnel.

Figure 11:
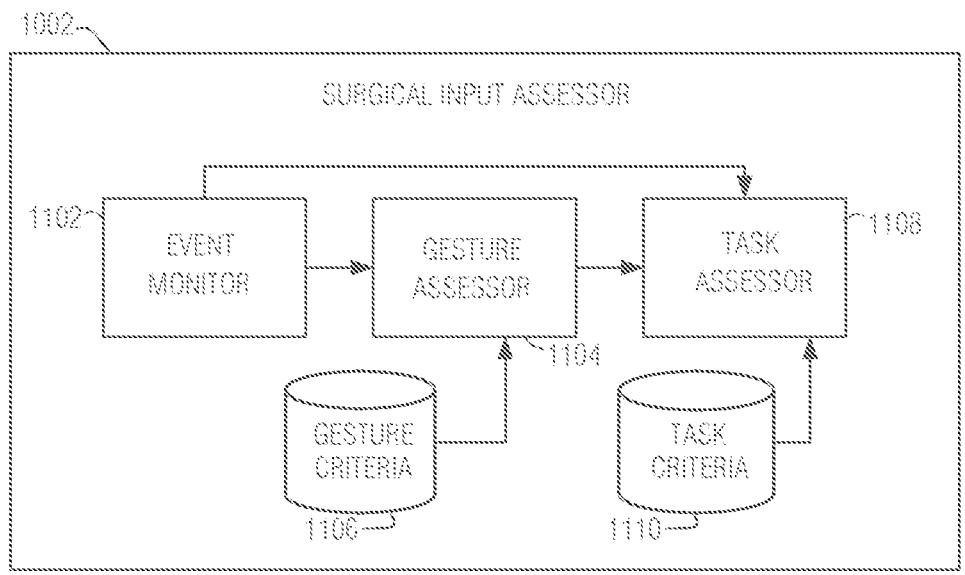
FIG. 11 is a diagram illustrating operational components, and their interactions, of surgical input assessor of the virtual surgical environment of FIG. 10, according to an embodiment.

FIG. 11 is a diagram illustrating operational components of surgical input assessor 1002, and their interactions, according to an embodiment. Event monitor 1102 receives event data, which can include system events, kinematics and external inputs, from TSS 950, and logs sequences of events. In a related embodiment, event monitor 1102 receives information regarding additional actions taken in surgical environment 902 other than with or by TSS 950, such as actions by assistant(s) or other equipment/instruments associated with the procedure. These actions may be detected by one or more sensors of the TSS 950, or by environment-monitoring sensors such as a video capture device, or by those other equipment/instruments themselves, and communicated to TSS 950, for instance. As referenced above, events can further include any of activations of instrument controls, such as, for example, button presses, instrument movement controls, instrument selections, video system controls, wrist movements, camera movement activations, master gestures/activations and other inputs provided by the surgeon, by assistants, or any other detectable actions/inputs/outputs. For example, other data that may be gathered as events include kinematics data, eye movements, user authentication (e.g., iris recognition), muscle activity (e.g., measured using an electromyography), sensed surgeon posture, images taken by an endoscope, system state (e.g. docked/deployed states of various instruments, engagement/disengagement state of the arms with a master controller, instrument types installed, quantity of instruments installed, head engagement state of the operator, forces applied to the controls such as master control, forces detected by the robot instruments, camera movement and control, touchscreen input, personnel location (e.g., as provided by sensors are in the surgical environment, and history of any of these. The sequences of events can be recorded as time-series data, and collectively, and can represent the coordinated actions of the operator(s) of TSS 950 and any personnel in the surgical environment 902, and/or any other data compiled from the surgical environment 902.

In some embodiments, a gesture assessor 1104 reads the time-series event data, and applies gesture criteria 1106 to ascertain whether combinations of events constitute any defined gestures. In the present context, a gesture is a sequence of two or more events that constitute compound movements of tools and controls. As an illustrative example, a single stitching motion associated with a suturing task may be regarded as a gesture. In this example, there is generally a sequence individual movements for which control input data may be collected and classified to recognize the gesture. In one embodiment, gesture criteria 1106 includes a library of sequences of events that constitute various gestures. In a more basic environment, gesture criteria 1106 may simply define a time window of recent events (e.g., most recent 40 seconds), such that for every time increment, a time window of sequences of events are considered to be a gesture. The time windows, or gestures in the present example, may overlap with other gestures.

Notably, in other embodiments, gesture assessor 1104 is not present; rather, the monitored events are fed to task assessor 1108. In yet another type of embodiment, where gesture assessor 1104 is available, a combination of detected gestures, and monitored events, is fed to task assessor 1108 in parallel.

Task assessor 1108 is programmed, or otherwise configured, to assess a current surgical task being performed. In the present context, a task is a series of events, gestures, or a combination thereof, that together produce a defined surgical effect. The task can be a clinically generic operation (e.g., incision task, suturing task, etc.) or a clinically-relevant step(s)/segment(s) of a procedure (e.g., UV anastomosis of a prostatectomy). Task assessment is based on a series of recent events, and based further on data from task criteria database 1110, which associates certain defined series of events with tasks. In a related embodiment, task criteria database 1110 may also include a library of surgical procedures where those tasks are commonly performed. In this type of embodiment, the identification of surgical procedure may itself be an input into the task-assessment algorithm. A surgical procedure in this context is a high-level descriptor such as, for instance, prostatectomy, umbilical hernia repair, mastectomy, or the like.

In various embodiments, gesture assessor 1104 and task assessor 1108 may individually perform one or more classification operations, such as K-nearest-neighbor (KNN) classification, for instance, clustering operations, such as K-means clustering, association rule mining operations, support vector machine (SVM) operations, an artificial neural network (ANN) operations (e.g., recurrent neural networks, convolutional neural networks, etc.), or the like, based on the respective criteria 1106, 1110 used as training-set data where applicable.

Events, gestures, and tasks may each have varying parameter values, such as joint angles, velocity, preceding/subsequent idling, and the like. It will be appreciated that during a teleoperated surgical procedure, control inputs can occur that cause changes in surgical system actuation state. For instance, a surgeon may move his or her head into and out of the viewer resulting in a change in head-in state. A surgeon may move his or her hands or feet in and out of contact with control inputs resulting in a change in following state, for example. A combination of instruments in use may be changed, resulting in a change in instruments type state, for example.

Operation of the TSS 950 in support of a surgical activity in the one or more surgical states additionally results in generation of control input information within a surgical system that indicates instrument motion, which is indicative of the actual manner in which a surgeon performed the surgical activity. For example, a surgeon may have used the control inputs to move an instrument rapidly or slowly, for example. A surgeon may have caused a surgical instrument to move in a direction toward or in a direction away from an anatomical structure along one or another path, for example. A surgeon, before actuating a particular instrument, may have adjusted a position of a different instrument using control inputs, for example.

Figures 19A, 19B, 19C:
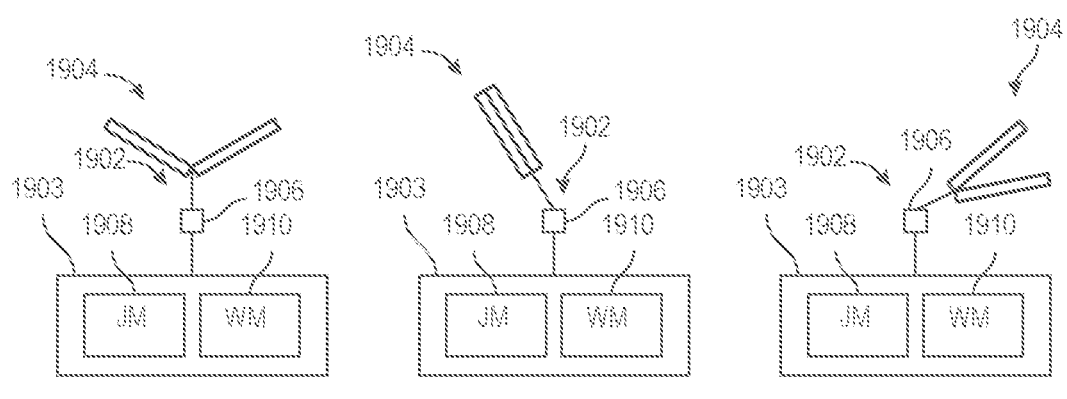
FIGS. 19A-19C are illustrative diagrams showing an example surgical instrument and an actuator assembly in which the surgical instrument is shown in different example surgical instrument actuation states in accordance with some embodiments.

FIGS. 19A-19C are illustrative diagrams showing an example surgical instrument 1902 and an actuator assembly 1903 in which the surgical instrument is shown in three different example surgical instrument actuation states in accordance with some embodiments. The example instrument 1902 includes a jaw end effector 1904 that can transition between open and closed states and a continuum of partially opened/partially closed states in between. The example instrument 1902 also includes a two degree of freedom (2-dof) wrist 1906 that can move between different two-dimensional (x, y) positional states. The example actuator assembly 1903 includes a first actuator 1908, which in some embodiments includes a jaw motor (JM) used to actuate the jaw end effector 1904. The example actuator assembly 1903 includes a second actuator 1910, which in some embodiments includes a wrist motor (WM) used to actuate the wrist 1906. During a surgery, the surgical instrument 1902 may transition through multiple instrument actuation states corresponding to different activities during a surgical procedure. Each transition results in generation of control input information that is captured and stored by event monitor 1102 and that is indicative of motion of the instrument as it is commanded to transition from its physical location and disposition (e.g., open or closed) in one state to its physical location and disposition in a next state.

As represented in FIG. 19A, for example, a first gesture may involve the first actuator 1908 (the JM) disposing the jaw end effector 1904 to a fully open state and the second actuator 1910 the (WM) disposing the wrist 1906 to a first positional state (x1, y1). As represented in FIG. 19B, for example, the surgical procedure may involve a second gesture in which the first actuator 1908 transitions the jaw end effector 1904 to a fully closed state and the second actuator 1910 transitions the wrist 1906 to a second positional state (x2, y2). As represented in FIG. 19C, for example, the surgical procedure may involve a third surgical activity in which the first actuator 1908 disposes the jaw end effector 1104 in a partially open/partially closed state and the second actuator 1910 transitions the wrist 1906 to a third positional state (x3, y3).

According to an embodiment, surgical input assessor 1002 cooperates with simulator 1006 to model the positional states in response to the control input information (e.g., events, gestures, or a combination thereof). The virtualized movements and positional states may in turn be assessed by task assessor 1108 to identify applicable tasks. In this type of embodiment, modeled kinematic information may be used to perform the task assessment, rather than, or in addition to, processed control input data.

Figure 12:
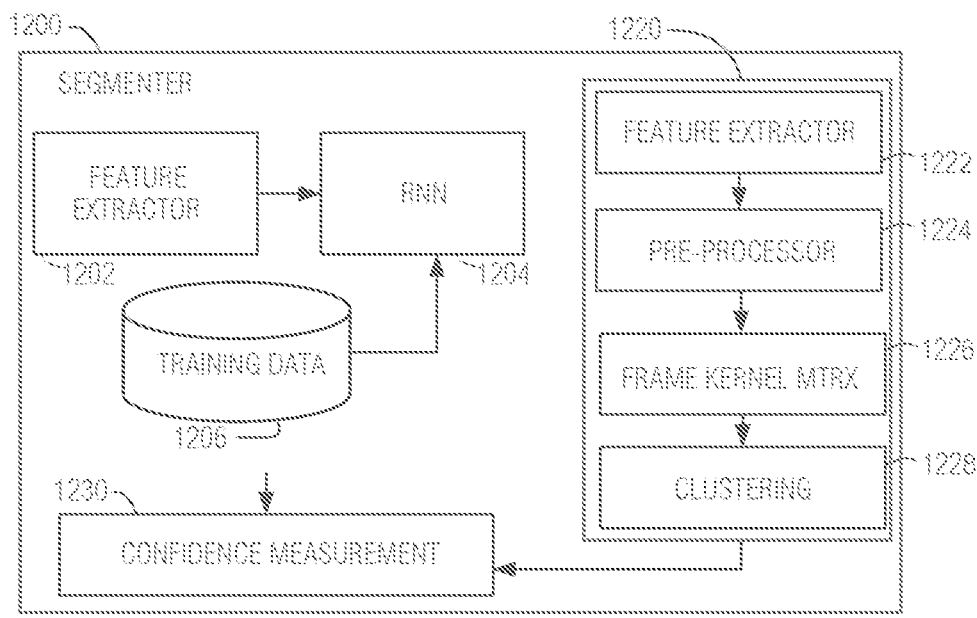
FIG. 12 is a diagram illustrating a segmenter, including its operational components and their interactions, of the virtual surgical environment of FIG. 10, according to an embodiment.

Turning now to FIG. 12, segmenter 1004 is depicted in detail, including its operational components and their interactions, according to an illustrative embodiment. In the example shown, segmenter 1004 is configured to selectively apply one of two classes of algorithms for segmentation assessment, namely, a real-time segmentation assessor 1200, and a post-processing-based segmentation assessor 1220.

Real-time segmentation assessor 1200 may be applied intra-operatively to make a segmentation assessment with negligible latency insofar as the surgeon or medical personnel may perceive. In an example embodiment real-time segmentation assessor 1200 is configured as a recurrent neural network (RNN), using a long short-term memory (LSTM) RNN architecture for deep learning. As depicted, feature extractor 1202 applies filtering or other selection criteria to a sequence of assessed tasks and their corresponding parameters to create a feature vector as the input to RNN 1204. An example of a feature vector may include a pose (e.g., position and rotation matrix information), along with a joint angle of an actuator, and velocity. RNN 1204 may be a bi-directional RNN, in which there are actually two RNNs, one forward-looking, and the other backward-looking. Accordingly, predicted future values and past values are taken into account in the RNN algorithm. In an example embodiment, RNN 1204 has two layers, a bidirectional LSTM, and a gated recurrent unit (GRU) layer, with hidden nodes in each layer.

Training data 1206 contains classified feature vectors that are used to train RNN 1204 using a suitable training algorithm, as will be recognized by persons having skill in the relevant art. The training data may be based on surgical input (e.g., events including control input parameters from surgeon-operated controls, or assistant-modifiable instrument configuration, events occurring in the surgical environment, etc.). In a related embodiment, the training data may be based on simulated effects of surgical input. In this latter type of embodiment, the simulator 1006 may be a source of training data.

Post-processing segmentation assessor may be applied at any point following an operation using all data recorded from the operation to make a segmentation assessment. In an example of a post-processing-based segmentation assessor 1220, clustering is performed using a hierarchical-aligned clustering algorithm (HACA) according to the embodiment depicted. An example segmentation assessor 1220 architecture includes a feature extractor 1222, pre-processor 1224, frame kernel matrix 1226, and clustering engine 1228 according to the embodiment depicted. The feature extractor 1222 produces feature vectors having a particular dimensionality and representing a specific set of parameters. Pre-processor 1224 may use a K-means clustering algorithm according to an embodiment.

Frame kernel matrix operation 1226 computes a self-similarity (or Gram) matrix, $K=\varphi(X)^T\varphi(X)$, relevant to motion segmentation, where each entry, $s_{ij}$ defines the similarity between two samples $x_i$ and $x_j$ by means of a kernel function:

$$k_{ij} = \exp\left(-\frac{\|x_i - x_j\|^2}{2\sigma^2}\right).$$

HACA Clustering engine 1228 performs a HACA algorithm consistent with Zhou, Feng, Fernando De la Torre, and Jessica K. Hodgins, "Hierarchical aligned cluster analysis for temporal clustering of human motion." IEEE Transactions on Pattern Analysis and Machine Intelligence 35, no. 3 (2013): 582-596.

In a related embodiment, post-processing-based segmentation assessor 1220 is employed post-operatively to update the training data 1206 and to re-assess the segmentation determinations of real-time segmentation assessor 1200.

Confidence measurement engine 1230 is programmed, or otherwise configured, to compute a confidence score representing a probability of correct segmentation. The confidence score may be computed with cross-entropy and log-probability computations. As will be described in greater detail below, the computed confidence may be used as a metric for evaluating surgeon skill, or as a weighting to other metrics, such as time, to further enhance assessment accuracy.

Figure 13:
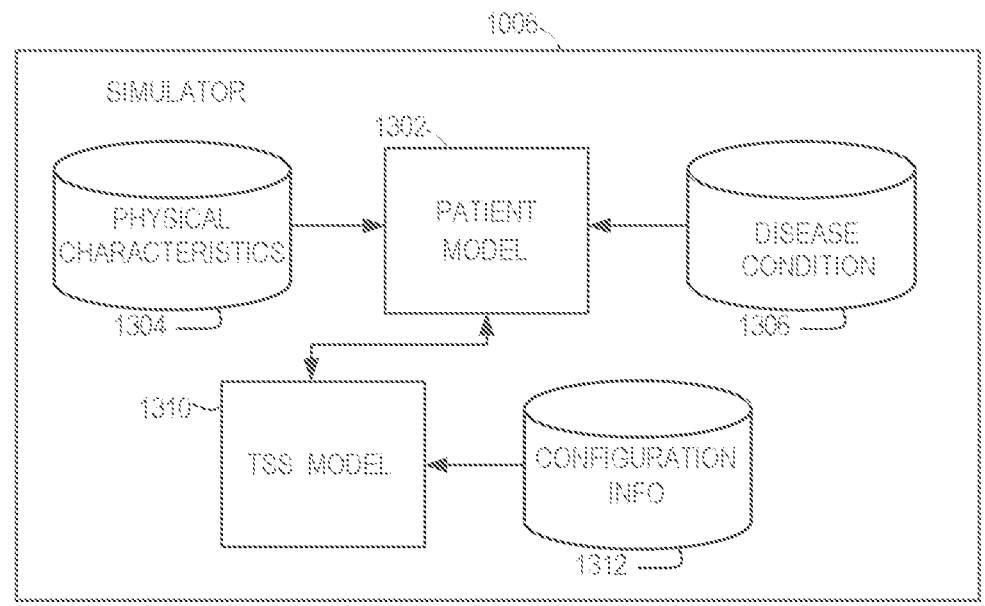
FIG. 13 is a diagram illustrating operational components, and their interactions, of a simulator of the virtual surgical environment of FIG. 10, according to an embodiment.

FIG. 13 is a diagram illustrating operational components, and their interactions, of simulator 1006 according to an embodiment. Patient model 1302 is programmed, or otherwise configured, to represent the patient based on the patient's measured or assessed physical characteristics 1304, and on a measured or diagnosed disease condition 1306. An example of relevant physical characteristics 1304 include size, weight, gender, age, body mass index (BMI), muscle tone, size and position of an organ, and the like, as well as any imaged anatomical structures, such as those obtained in a CT scan, MRI, ultrasound, or other test. Similarly, disease condition 1306 may include such features as tumors, cysts, hernias, tom connective tissue, fractured bones, and the like. TSS modeler 1310 is programmed, or otherwise configured, to represent TSS 950, including the tools, end effectors, and other configured portions, as represented by configuration information 1312. TSS modeler 1310 receives control input information from TSS 950 so that the positioning and movements of the various surgical tools may be reflected in the virtual surgical environment.

TSS modeler 1310 and patent model 1302 may exchange state information during simulation as a virtual surgical procedure is simulated. Accordingly, one or both of these engines may maintain and update a current state of the patient as changes are effected by way of the surgical procedure.

In one embodiment, simulator 1006 is operated along-side surgical environment 902 to track the progress of TSS 950 and of the patient during a surgical procedure. In another embodiment, a given segment of a surgical procedure may be initiated for simulation at the request of the surgeon, or in response to a trigger. This intra-operative simulation may be called for if a surgeon encounters a critical or difficult moment in the procedure, and wishes to practice certain movements or various techniques before deploying those actions on the patient for real. In a related embodiment, a parallel-running simulation may be autonomously analyzed to determine the current surgical stage using segmenter 1004, which may be further trained with model-based situational data in a set of feature vectors.

In another embodiment, simulator 1006 may be used for surgical training or practice in lieu of an actual patient. In some implementations, the user-interfaces of TSS 950 for the surgeon and other medical personnel may be used to realistically simulate the surgical environment and to provide machine-interface experience as part of the training or practice exercise.

Surgeon Assessment

Figure 14:
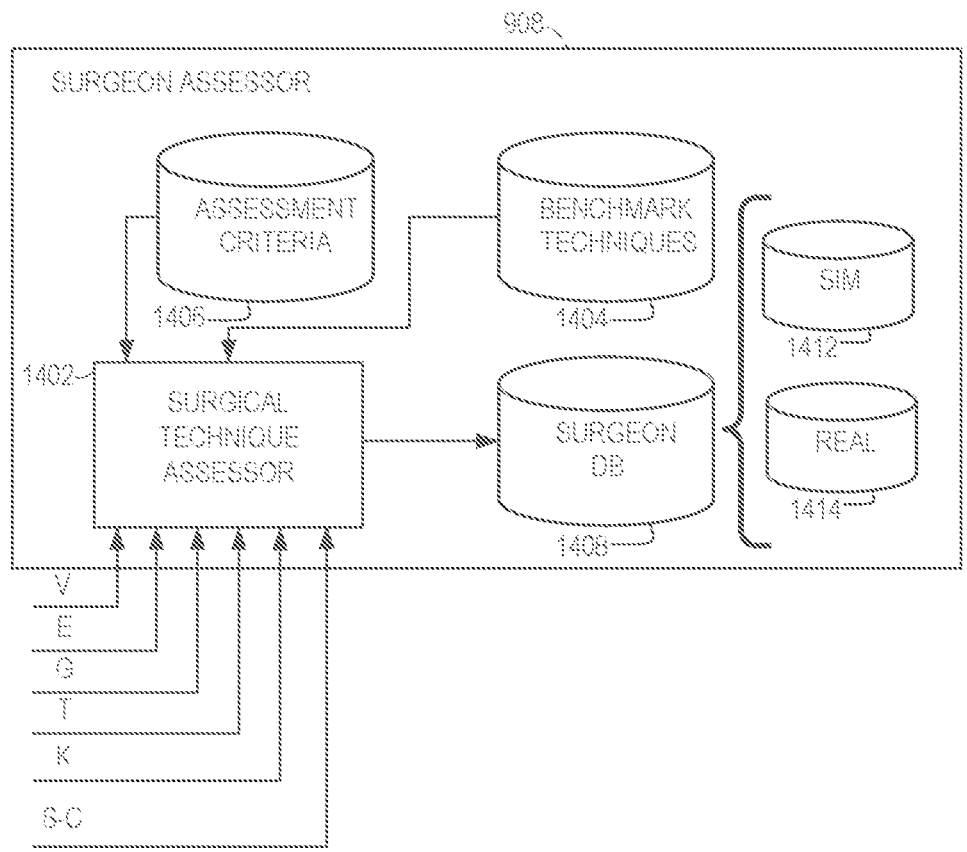
FIG. 14 is a diagram illustrating operational components, and their interactions, of a surgeon assessor of the system of FIG. 9, according to an embodiment.

FIG. 14 is a diagram illustrating operational components, and their interactions, of surgeon assessor 908 in greater detail according to an embodiment. At the heart of surgeon assessor 908 is surgical technique assessor 1402, which is programmed, or otherwise configured, to analyze control inputs signaling, and the assessments by gesture assessor 1104 (where available), task assessor 1108, as well as segmenter 1004, to produce an assessment or score representing the quality of surgical performance of a surgeon operating the control inputs of TSS 950, whether they may be used during a surgical procedure, or during simulation for practice or training.

Inputs to surgical technique assessor include video information V, event information E, gestures G, and assessed tasks T, along with kinematic data K. This data may be provided by TSS 950, or VSE 904 (e.g., from surgical input assessor 1002, and simulator 1006). In a related embodiment, the inputs may include a segmentation confidence score S-C, as determined by confidence measurement engine 1230 of segmenter 1004 based on segmentation determinations by RNN 1204, or clustering engine 1228.

A segment corresponds to a surgical procedure portion and is defined in terms of a combination of one or more features representing a combination of one or more of video, events, gestures, tasks and kinematics. A segment includes a combination of events/kinematics/video that can be represented as gestures/tasks or that can be represented directly without the intermediate gestures/tasks representations.

In an embodiment, surgical technique assessor 1402 computes various statistics for each of a variety of temporal and spatial metrics. For instance, a time duration of various surgical procedure segments may be assessed. Likewise, task-level time durations may be computed and aggregated in some fashion, per segment, for example. An economy-of-motion analysis may also be performed, which examines a quantity of gestures or other movements, quantity of events, or some combination of these quantities, associated with completion of certain tasks or surgical segments. Idle time (i.e., the absence of movement) may also be taken into account. Other metrics, such as velocity of motion, input-device wrist angles, idle time (e.g., stationarity), master workspace range, master clutch count, applied energy, and other such parameters, may also be taken into account in assessment of surgical technique. Camera control metrics, such as camera movement frequency, camera movement duration, cameral movement interval also may be taken into account in assessment of surgical technique. In some embodiments, camera clutch movement (CMFrq) is defined as the average number of endoscope movements made by a surgeon per time increment (e.g., per second) over the course of an entire event or segment; camera movement duration (CMDur) is defined as the average time increments (e.g., seconds) of all endoscope movements over the course of an entire event or segment; and camera clutch interval (CMInt) is defined as the average time increment (e.g., in seconds) between endoscope movements over the course of an entire event or segment. By way of non-limiting example, duration of use of the camera, consistency of camera use, duration of energy application (e.g. cutting tissue, cauterizing tissue, augmenting applied energy), frequency of use of the master clutch, temporal control of different arms (e.g., duration between use of arm 1 and arm 3), frequency of master alignment with end effector orientation, and the like.

Assessment criteria 1406 defines one or more criteria for computing a performance assessment of the surgeon. In one type of embodiment, a performance of a surgical procedure is given a series of scores corresponding to the different identified stages of the procedure. Assessment criteria 1406 may include filtering, masking, and weighting information to be applied to the various metrics in order to adjust their relative importance. Notably, different weights/adjustments may be applied to the metrics for different surgical procedures or for different stages of a given surgical procedure. Also, assessment criteria 1406 may define an algorithm or formula(s) to be applied in rendering the surgical performance assessment. In an embodiment where surgical technique assessor 1402 uses a machine-learning algorithm, such as an ANN, classifier, clustering agent, support vector machine, or the like, assessment criteria 1406 may include criteria for constructing feature vectors of metrics.

Benchmark techniques database 1404 includes scores and metrics achieved by surgeons or other medical personnel deemed to be experts at corresponding surgical procedures.

For example, in some embodiments, the benchmark database 1404 includes benchmarks for surgeon skill level based upon camera control times. The inventor conducted a study in which camera control times were measured for each of multiple exercises representing different surgical tasks (e.g., camera targeting, dots and needles, energy dissection, match board, needle targeting, peg board, pick and place, ring and rail, ring walk, scaling, suture, sponge, thread the rings, and tubes) for surgeons rated as experienced, intermediate or novice in use of teleoperated surgical systems (TSSs). The results of the exercises are used to create benchmarks for surgeon skill level based upon camera control times. The study found that experienced surgeons generally perform camera control significantly faster than new surgeons. Intermediate surgeons more often than not performed exercises significantly faster than new surgeons. However, the study found no significant differences in exercise completion time between intermediate and experienced surgeons.

The study revealed a number of surprising findings. For example, it was found that experienced surgeons had significantly higher CMFrq than new surgeons for most exercises, that intermediate surgeons had significantly higher CMFrq than new surgeons for most exercises and that there were no significant differences in CMFrq between intermediate and experienced surgeons. The study also found that experienced surgeons had significantly shorter CMDur than new surgeons for most exercises. In most exercises, intermediate surgeons had significantly shorter CMDur than new surgeons. In most exercises, experienced surgeons had significantly shorter CMDur than intermediate surgeons. In most exercises, experienced surgeons had significantly shorter C MInt than new surgeons whereas intermediate surgeons had significantly shorter CMInt than new surgeons in most exercises. There were no significant differences in CMInt between intermediate and experienced surgeons.

In a related embodiment, feature vectors constructed per task or per segment, which may also be done in real time, for a given procedure are compared against one or more benchmark scores corresponding to the task or segment of the surgical procedure. The comparison may be a simple Cartesian distance measure between the feature vector in question and the benchmark feature vector, or some other measure of similarity. The determined degree of similarity may be returned as a surgical performance score corresponding to the task, segment, etc.

The various scores computed for a given surgical procedure for each surgeon is stored in surgeon database 1408. Scores over time may be analyzed to detect any trends, such as a rate of improvement as the surgeon gains experience and expertise in the use of TSS 950, and in performing certain procedures. According to some embodiments, surgeon database 1408 distinguishes performance scoring between simulation-only operation of TSS 950 at 1412, from those corresponding to procedures performed on real patients at 1414.

Data Logging

Figure 15:
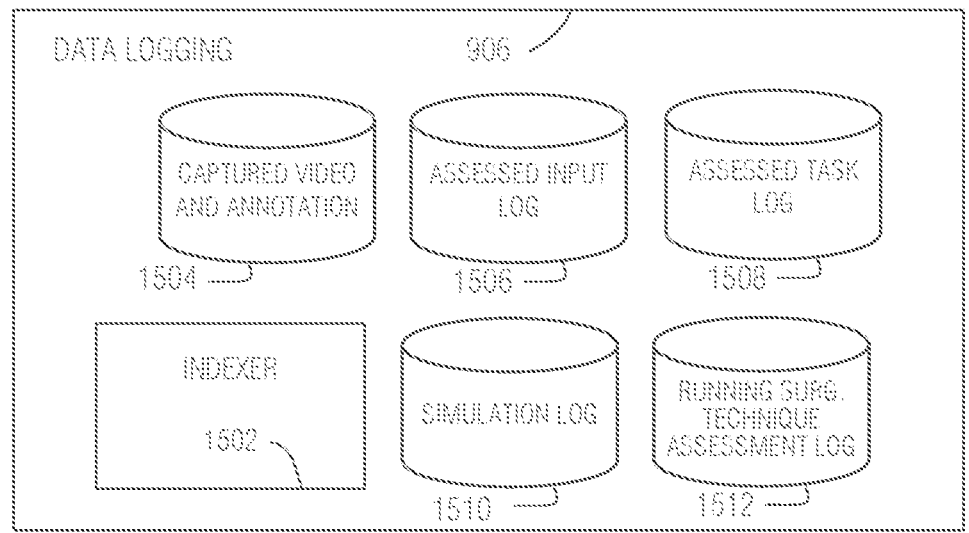
FIG. 15 is a diagram illustrating operational components, and their interactions, of a data logging system of the system of FIG. 9 according to an example embodiment.

FIG. 15 is a diagram illustrating operational components, and their interactions, of data logging system 906 according to an example embodiment. Indexer 1502 is programmed, or otherwise configured, to associate incoming data with other relevant data to facilitate data retrieval. In the example depicted, a variety of data may be logged during a surgical procedure. For example, captured video and any added annotations 1504, assessed input log 1506, assessed task log 1508, simulation log 1510, and running surgical technique assessment log 1512. Each item of data may be further associated with the date and time of its capture, the patient, the surgeon, the TSS, the procedure type, and other relevant data.

In an embodiment, for captured video and annotation data 1504, indexer 1502 may break the videos into segments corresponding to assessed segments of the surgical procedure. Assessed input log 1506 stores time-series events and other input information, as well as assessed gestures. Assessed task log 1508 contains assessments of tasks and surgical procedure segments that were performed in real time. In an embodiment, assessed input log 1506 includes a short-term storage portion and a long-term storage portion, with the short-term storage portion storing all incoming input information, including events; whereas the long-term storage portion stores only those inputs upon which task-determination decisions have been made.

Simulation log 1510 contains time-series state information describing patient model 1302 and TSS modeler 1310 of simulator 1006. In an embodiment, the sampling rate of simulation log is similar to the rate at which the segmentation assessment is performed (for example, 4-20 samples per second). Sufficient data is logged to enable a detailed review and analysis of a performed surgical procedure.

Running surgical technique assessment log 1512 stores time-series samples of a constantly-updated surgeon performance scoring produced by surgical technique assessor 1402. The data logged in running surgical technique assessment log 1512 may be specific to a current surgical procedure (or simulation) being performed on a current patient. This data set may overlap with data in surgeon database 1408 (FIG. 14), which stores surgeon-specific data across multiple different patients, procedures, and dates.

Assist Engine

Figure 16:
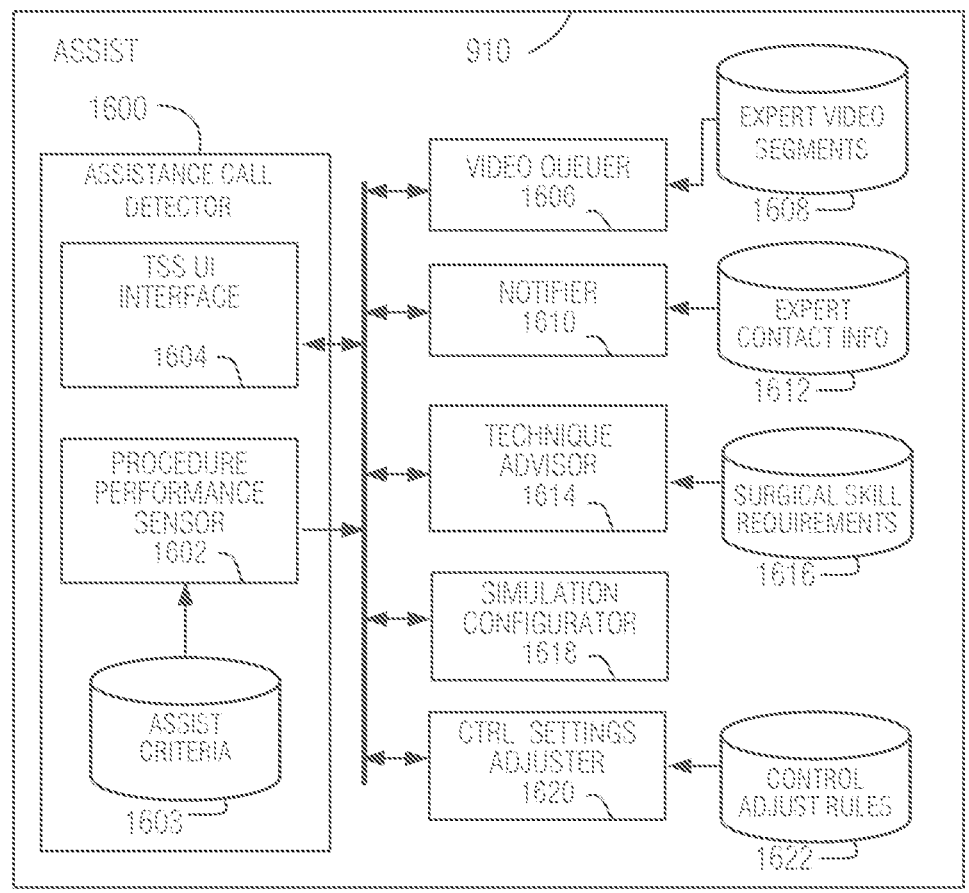
FIG. 16 is a diagram illustrating operational components, and their interactions, of an assist engine of the system of FIG. 9 according to some embodiments.

FIG. 16 is a diagram illustrating operational components, and their interactions, of assist engine 910 according to some embodiments. As depicted, assist engine 910 includes an assistance call detector 1600 that is programmed, or otherwise configured, to detect a call for surgeon assistance. In some embodiments, assistance call detector 1600 procedure performance sensor 1602 and TSS user interface (UI) interface 1604, either of these engines may initiate an assist operation of assist engine 910 in response to their respective input. Procedure performance sensor 1602 monitors the operation of VSE 904 and surgeon assessor 908. For example, the output of segmenter 1004, overlaid with the running surgical technique assessment (e.g., as logged in database 1512), provides information on the stage of the surgical procedure, and a measured performance of the surgeon at that stage.

Assist criteria 1603 includes various threshold conditions that, when met, trigger the operation of assistive action by one or more of the assistance rendering engines described below. Notably, different thresholds may be associated with different types of assistance. In operation, procedure performance sensor 1602 compares the current running surgical technique assessment for the current surgical procedure and segment thereof, against a threshold condition corresponding to the procedure and stage. If the threshold condition comparison is met—i.e., if the current running surgical technique assessment score falls below any given threshold, corresponding assistance may be offered and/or provided.

In related embodiments, the threshold condition of assist criteria 1603 may also be surgeon-specific, or patient specific. For instance, a relatively more experienced surgeon may configure the system with a higher threshold before assistance is offered, than a more novice surgeon. Likewise, a lower threshold may be selected for surgery on a patient in a more critical condition (e.g., serious trauma patient, a patient of advanced age, a newborn or pre-term patient, etc.).

Additionally, for example, the assist criteria 1603 could be used to selectively request input from particular expert surgeons with expertise in particular step of a procedure. For example, certain surgeons may be really good at complicated dissections and therefore they should be the ones "on-call" if someone struggles with that step whereas other surgeons can be called for simpler steps.

TSS UI interface 1604 exchanges information with the surgeon's console of TSS 950. TSS UI interface 1604 may receive a request from the surgeon for specific assistance, in which case, TSS UI interface may command an assistance rendering engine to provide corresponding assistance. Context-relevant assistance information may likewise be displayed to the surgeon via TSS UI interface feeding that information to the surgeon's console.

In a related embodiment, in response to the automated call for assistance by procedure performance sensor 1602, TSS UI interface 1604 provides a visual or audible notification to the surgeon offering that assistance, and providing a control input for the surgeon to accept, reject, or postpone the assistance.

According to the embodiment depicted, a number of different assistance rendering engines are available to provide corresponding types of assistance for the surgeon or other medical personnel. In various other embodiments, more or fewer assistance rendering engines are provided. As depicted, video queuer 1606 is configured to retrieve video segment(s) from database 1608 for playback. The video segments may have particular correspondence to the current stage of the surgical procedure, as determined by segmenter 1004. For instance, the video segment to be queued may represent the current stage of the surgical procedure, or an upcoming stage.

Notifier 1610 is configured to initiate communications with an on-call surgeon according to expert contact info 1612, who, via a remote console or other interface, can provide direct guidance and/or assistance to the surgeon.

Technique advisor 1614 may recommend a particular surgical technique to be used in a given scenario, in response to the current or upcoming surgical stage and taking into account the assessed running surgical technique assessment of the surgeon, based on surgical skill requirements database 1616. In a related embodiment, technique advisor 1614 may provide applicable prompting or other instructions or recommendations to other medical personnel, such as to one or more assistants in the surgical environment.

In a related embodiment, technique advisor 1614 includes a prediction function that predicts an upcoming surgical stage based on duration of steps, order of steps, performance level of steps—all based on current segment and surgeon performance, as well as optionally on historical data corresponding to that surgeon. This information can be used to forecast future events, such as the end of the procedure for optimal OR turnover, an upcoming instrument exchange, etc.

Simulation configurator 1618 is operative to autonomously set up a simulation scenario to be executed by simulator 1006 corresponding to a current or upcoming surgical procedure stage. This type of assistance may allow the surgeon to practice a certain technique in a virtual surgical environment, intraoperatively, before returning to the actual surgical environment and performing the technique on the patient.

Control settings adjuster 1620 is operative to automatically vary one or more behaviors of the TSS in response to control input in order to facilitate a surgical task. The adjustment may be done in accordance with control adjustment rules 1622, which may be procedure-specific, task-specific, surgeon-specific, or some combination thereof. Examples of variable TSS behaviors include control-input sensitivity adjustment (e.g., reduction in motion velocity for a given input event or gesture), gesture filtering (e.g., allowing certain input movements to cause a surgical effect, but not others), adjustments to video capture settings, etc. Other adjustments include camera horizon/zoom/position, table position, image properties (color, hue, overlays, etc.), loading of pre-op images for the current/upcoming step from current patient or related patients, master-tool motion scaling, force feedback gain, mapping of control input button presses to be different depending on situation/segment, or some combination thereof.

Figure 21A:
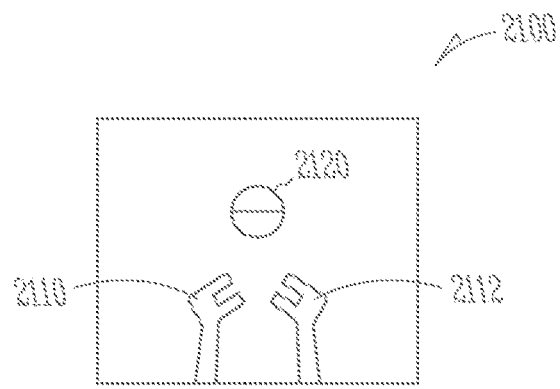
FIGS. 21A-21C are illustrative drawings showing surgical scene horizon changes effected by a control settings adjuster of the surgeon assessor of FIG. 14 to assist a surgeon in achieving a viewpoint in which the surgeon can more accurately control surgical instruments within a surgical scene of a TSS.
Figure 21B:
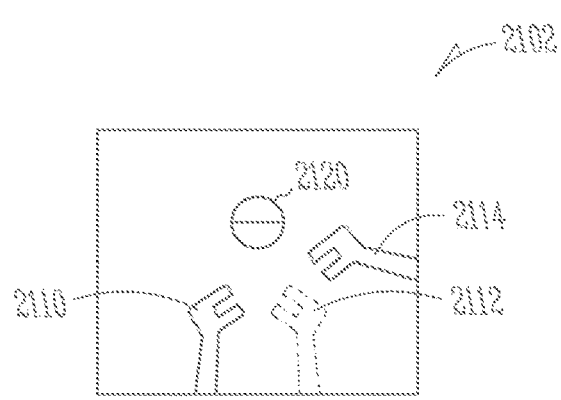
Figure 21C:
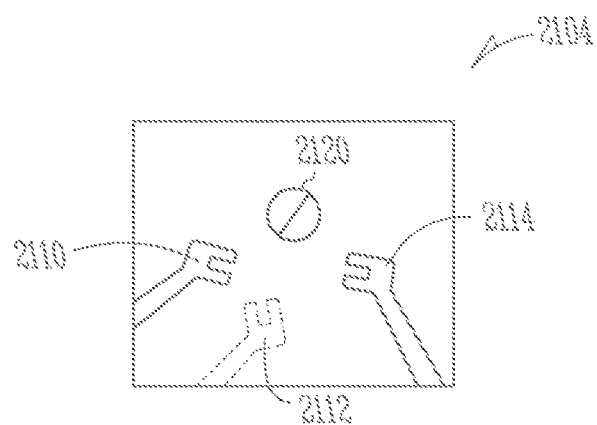

FIGS. 21A-21C are illustrative drawings showing surgical scene horizon changes effected by the control settings adjuster 1620 to assist a surgeon in achieving a viewpoint in which the surgeon can more accurately control surgical instruments within a surgical scene of a teleoperated surgical system (TSS). A surgeon views a surgical scene including surgical instruments stereoscopically through the left eye display 32 and a right eye display 34 (note that while a stereoscopic surgeon view is depicted and described for exemplary purposes, in various other embodiments, a monoscopic view can be provided). Assume, for example, that a TSS mounts three different surgical instruments 2110, 2112, 2114, plus an endoscope-mounted camera (not shown). The surgeon can control the surgical instruments and the endoscope two at a time using the left and right handgrip control inputs 36, 38. Instruments that are within the field of view of the camera are visible to the surgeon within the surgical scene view. Further assume, for example, that the surgeon changes instruments during a transition from one task to the next a surgeon changes. Moreover, assume that the changed from instrument is positioned at a different location within the surgical scene than the changed to instrument. In that case, although the surgeon's grip on the left and right handgrip control inputs 36, 38, is unchanged, the location and orientation of the surgical instrument within the surgical scene that currently is under the surgeon's control has changed. The control settings adjuster 1620 can provide adjustment of the surgical scene horizon so as to reconcile the surgeon's viewpoint of instruments currently under surgeon control within a surgical scene with the surgeon's hand positions on the left and right handgrip control inputs 36, 38 in order to improve or optimize the accuracy and control of the surgical instruments.

Referring to FIG. 21A, there is shown a first surgical scene 2100 having a first horizon indicated by an orientation of a horizon icon 2120 that includes first and second surgical instruments 2110, 2112 currently under a surgeon's control. A horizon icon 2120 can be displayed as an optional overlay within the screen indicates a surgical scene horizon that is "level"—typically when the endoscope is in a neutral position in the manipulator on the patient side cart. It will be understood that level horizon is nominally defined as the neutral position within the patient side arm—not relative to the left and right displays since these never change position. Moreover, it will be appreciated that the orientations of the surgical instruments 2110, 2112 and the first surgical scene horizon shown in FIG. 21A are consistent with natural anatomical orientations of a surgeon's hands upon the left and right handgrip control inputs 36, 38 when viewing a scene located directly in front of the surgeon's eyes. Note that the 3D Cartesian positions of the surgeon's hands may be different than the 3D Cartesian position of the instruments due to the master clutch capability of the TSS.

Referring to FIG. 21B, there is shown a second surgical scene 2102 having the first horizon indicated by the orientation of the horizon icon 2120 that includes first and third surgical instruments 2110, 2114 currently under a surgeon's control. It is assumed that in course of transitioning from the first scene 2100 to the second scene 2102, the surgeon has changed from using the second surgical instrument (shown with dashed lines) 2112 to using a third surgical instrument 2114. Thus, the surgeon surgeon's hands upon the left and right handgrip control inputs 36, 38 control the first and third surgical instruments 2110, 2114 within the second surgical scene 2102 rather than controlling the first and second surgical instruments 2110, 2112 as they did in the first scene 2100. The second and third surgical instruments 2112, 2114 are positioned at different locations within the surgical scene. Moreover, the horizon icon 2120 indicates that the view of the second surgical scene 2102 from the perspective of the left and right eye displays 32, 34 is the same as the perspective was for the first scene 2100. Thus, the surgeon now controls the third instrument 2114, which is located in the second surgical scene 2102 at a different location from that of the previously controlled second instrument 2112. Although the surgeon's hand positions on the left and right handgrip control inputs 36, 38 may be unchanged and the surgical scene horizon is unchanged, the location of one of the currently controlled instruments, the third instrument 2114, is changed. Additionally, if the surgeon is required to mirror the pose of the third instrument 2114 before acquiring control over that instrument, the orientation of the right handgrip control input 38 would have to be changed to match the new orientation of the third instrument 2114 which is different than instrument 2112. For these and potentially other reasons, the positions of the surgical instruments 2110, 2114 and the second surgical scene horizon shown in FIG. 21B may not be consistent with natural anatomical positions of a surgeon's hands upon the left and right handgrip control inputs 36, 38. As a result of this inconsistency, a surgeon may not be able to move the third instrument 2114 with the accuracy and/or dexterity that he or she otherwise could have.

Referring to FIG. 21C, there is shown a third surgical scene 2104 having a second horizon indicated by the orientation of the horizon icon 2120 that includes the first and third surgical instruments 2110, 2114 currently under a surgeon's control. The third scene 2104 is identical to the second scene 2102 except that the surgical scene horizon is changed as indicted by orientation of the horizon icon. It will be appreciated that as a result of the change in scene orientation, the positions/orientation of the surgical instruments 2110, 2114 and the third surgical scene horizon shown in FIG. 21C are more closely consistent with natural anatomical positions of a surgeon's hands upon the left and right handgrip control inputs 36, 38 when viewing a scene located directly in front of the surgeon's eyes. As a result of the change in orientation of the surgical scene horizon, a surgeon can more readily move the third instrument 2114 with greater accuracy than he or she could with the surgical scene horizon of the second scene 2102.

The control settings adjuster 1620 imparts changes in camera orientation control settings to the endoscope-mounted camera to change the horizon orientation from that shown in the second surgical scene 2102 to that shown in the third surgical scene 2104. The surgical technique assessor 1402 can determine, for example, that expert surgeons use the horizon orientation of the third scene 2114 when controlling instruments at the locations of the first and third instruments 2100, 2104 shown in the second and third scenes 2110, 2114. The control settings adjuster 1620 can implement such horizon orientation change automatically on behalf of a novice surgeon. Thus, for example, when a novice surgeon transitions to a task for which, according to expert surgeons' accuracy of instrument movement can be improved through a change in surgical scene horizon, the control settings adjuster 1620 can automatically change orientation of the surgical scene horizon to better correlate the surgical scene horizon orientation and instrument locations within the scene with a surgeon's hand positions on the left and right handgrip control inputs 36, 38.

Figure 22A:
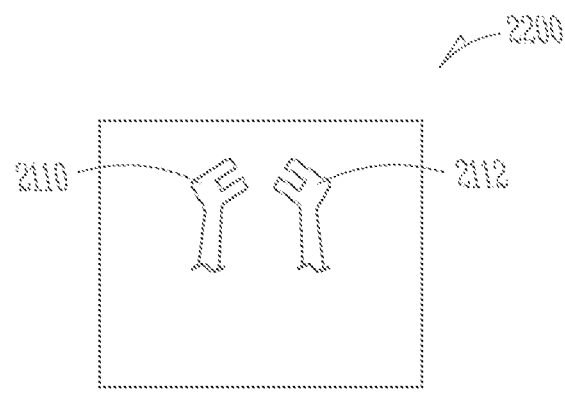
FIGS. 22A-22B are illustrative drawings showing surgical scene two-dimensional position changes effected by the control settings adjuster of the surgeon assessor of FIG. 14 to assist a surgeon in achieving a viewpoint in which the surgeon can better observe relevant information within a surgical scene of a TSS.
Figure 22B:
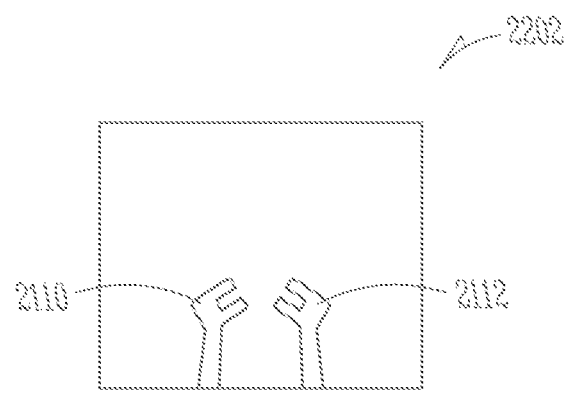

FIGS. 22A-22B are illustrative drawings showing surgical scene two-dimensional position changes effected by the control settings adjuster 1620 to assist a surgeon in achieving a viewpoint in which the surgeon can better observe relevant information within a surgical scene of a TSS. Referring to FIG. 22A, there is shown a fourth surgical scene 2200 in which the first and second surgical instruments 2110, 2112 have their end effector portions located near an edge of the surgical scene 2200. It will be appreciated that with the surgical instruments 2100, 2102 located near the scene edge as in the fourth surgical scene 2200, items of interest located near that scene edge, such as body tissue (not shown), might located outside of the visible scene, and therefore, not be visible to the surgeon. Referring to FIG. 22B, there is shown a fifth surgical scene 2202 in which the first and second surgical instruments 2110, 2112 have their end effector portions located nearer a center of the surgical scene 2202. The control settings adjuster 1620 imparts changes in camera control settings to the endoscope-mounted camera to change from the second surgical scene 2102, that displays a first two-dimensional region in which instruments end effectors are disposed at an edge of the scene, to the third surgical scene 2104 that displays a second two-dimensional region in which instruments end effectors are disposed near a center of the scene. The surgical technique assessor 1402 can determine, for example, that expert surgeons prefer that instruments be displayed in a particular region within a surgical scene, such as the center for example. Thus, for example, when a novice surgeon transitions to a task involving a scene, which according to expert surgeons, can be better viewed with a change in region of the scene portrayed so as to move the instruments toward the center of the scene, for example, the control settings adjuster 1620 can automatically change positions of the camera so as to change position of the instruments and tissue structures (not shown) portrayed within the scene.

Figure 23A:
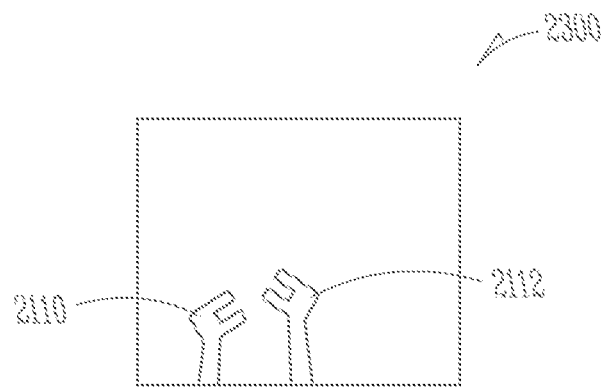
FIGS. 23A-23B are illustrative drawings showing surgical scene zoom level changes effected by the control settings adjuster of the surgeon assessor of FIG. 14 to assist a surgeon in achieving a viewpoint in which the surgeon can better observe relevant information within a surgical scene of a TSS.
Figure 23B:
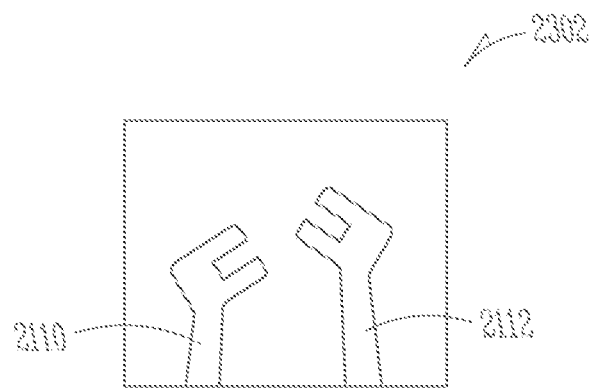

FIGS. 23A-23B are illustrative drawings showing surgical scene zoom level changes effected by the control settings adjuster 1620 to assist a surgeon in achieving a viewpoint in which the surgeon can better observe relevant information within a surgical scene of a TSS. Referring to FIG. 23A, there is shown a sixth surgical scene 2300 in which the first and second surgical instruments 2110, 2112 are shown zoomed-out so as to appear distant and small within the surgical scene 2200. It will be appreciated that the distant and small appearance of the surgical instruments 2100, 2102 in the sixth surgical scene 2300 also results in other items of interest, such as body tissue (not shown), with which the surgical instruments 2100, 2102 interact appearing distant and small, and therefore, difficult for the surgeon to see. Referring to FIG. 23B, there is shown a seventh surgical scene 2302 in which the first and second surgical instruments 2110, 2112 are shown zoomed-in so as to appear closer and larger and easier to see in detail. The control settings adjuster 1620 imparts changes in camera control settings to the endoscope-mounted camera to change from the fifth surgical scene 2300, that displays a first zoomed-out zoom level to the seventh surgical scene 2302 that displays a second zoomed-in zoom level. The surgical technique assessor 1402 can determine, for example, that expert surgeons prefer that instruments be displayed at a particular zoom level for particular tasks. Thus, for example, when a novice surgeon transitions to a task involving a scene, which according to expert surgeons, can be better viewed with a change in zoom level, for example, the control settings adjuster 1620 can automatically change zoom level of the camera.

Additionally, camera adjustments can involve estimates of a patient's anatomy position and orientation of the camera to optimize camera position/orientation for movements and interactions. For example, if a surgeon needs to drive a needle in a particular direction based on anatomy, the camera could align itself to this environmental cue.

In some embodiments, the assistance by any of these assist engines may be stage-synchronized to the current surgical procedure stage, based on the stage current assessment. As discussed above, stage synchronization refers to alignment in terms of surgical process flow, rather than strict temporal alignment. In some embodiments, stage synchronization supports stage-offsetting such that assistance may be provided to prepare the surgeon or surgical team for an upcoming stage of the surgical procedure.

The assistance may be further selected to match the assessed type of surgical technique being used, as assessed by segmenter 1004, simulator 1006, surgeon assessor 908, or by a combination including two or more of these engines.

Figure 17:
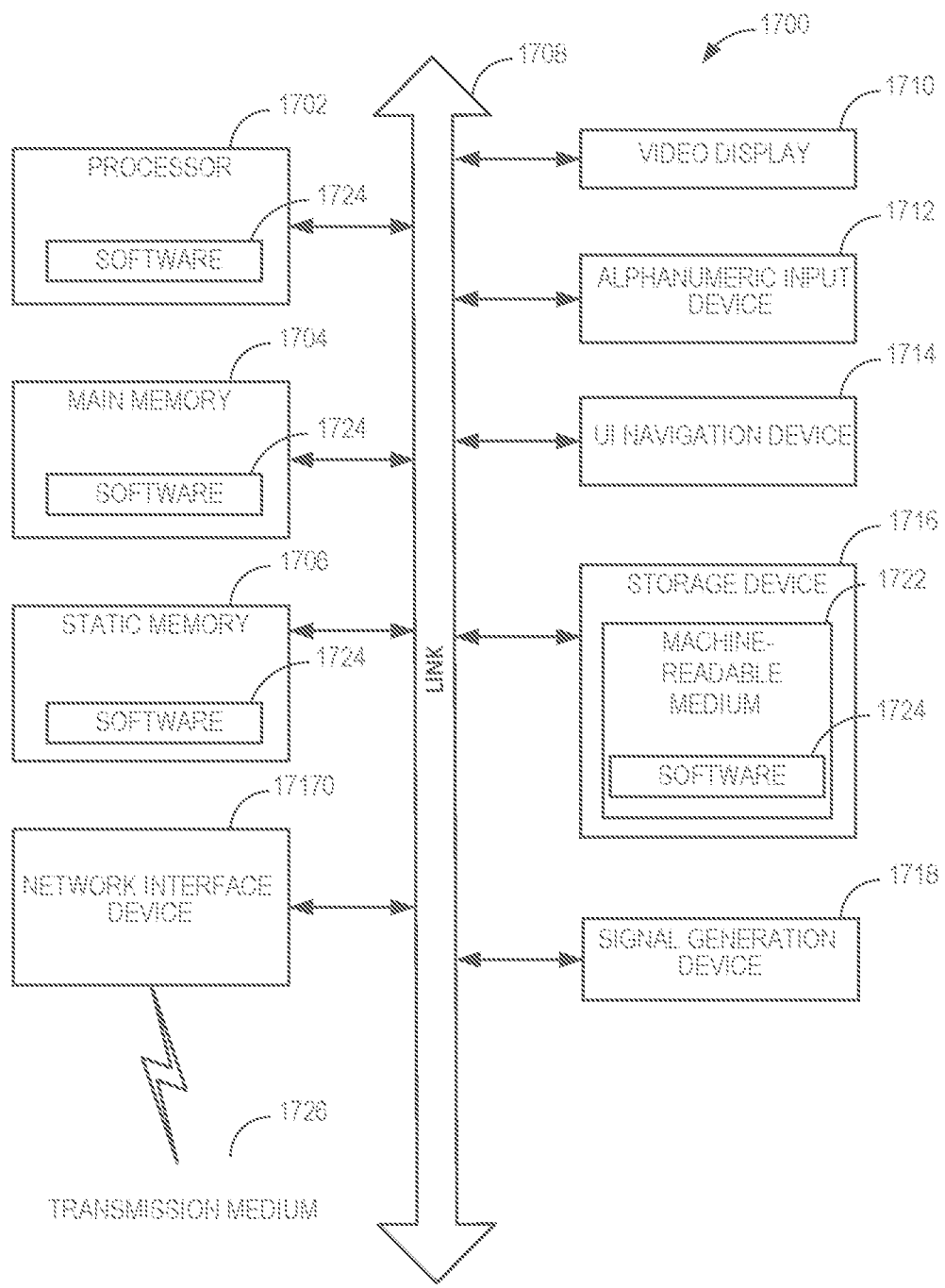
FIG. 17 is a block diagram illustrating a computer system in the example form of a general-purpose machine, which may be transformed into a special-purpose machine to carry out aspects of the embodiments described herein.

FIG. 17 is a block diagram illustrating a computer system in the example form of a general-purpose machine. In certain embodiments, programming of the computer system 1700 according to one or more particular operational architectures and algorithms described herein produces a special-purpose machine upon execution of that programming, to form VSE 904, data logging engine 906, surgeon assessor 908, assist engine 910, or any combination of these systems. In a networked deployment, the computer system may operate in the capacity of either a server or a client machine in server-client network environments, or it may act as a peer machine in peer-to-peer (or distributed) network environments.

Example computer system 1700 includes at least one processor 1702 (e.g., a central processing unit (CPU), a graphics processing unit (GPU) or both, processor cores, compute nodes, etc.), a main memory 1704 and a static memory 1706, which communicate with each other via a link 1708 (e.g., bus). The computer system 1700 may further include a video display unit 1710, an alphanumeric input device 1712 (e.g., a keyboard), and a user interface (UI) navigation device 1714 (e.g., a mouse). In one embodiment, the video display unit 1710, input device 1712 and UI navigation device 1714 are incorporated into a touch screen display. The computer system 1700 may additionally include a storage device 1716 (e.g., a drive unit), a signal generation device 1718 (e.g., a speaker), a network interface device (NID) 1720, and one or more sensors (not shown).

The storage device 1716 includes a machine-readable medium 1722 on which is stored one or more sets of data structures and instructions 1724 (e.g., software) embodying or utilized by any one or more of the methodologies or functions described herein. The instructions 1724 may also reside, completely or at least partially, within the main memory 1704, static memory 1706, and/or within the processor 1702 during execution thereof by the computer system 1700, with the main memory 1704, static memory 1706, and the processor 1702 also constituting machine-readable media.

While the machine-readable medium 1722 is illustrated in an example embodiment to be a single medium, the term "machine-readable medium" may include a single medium or multiple media (e.g., a centralized or distributed database, and/or associated caches and servers) that store the one or more instructions 1724. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

NID 1730 according to various embodiments may take any suitable form factor. In one such embodiment, NID 1720 is in the form of a network interface card (NIC) that interfaces with processor 1702 via link 1708. In one example, link 1708 includes a PCI Express (PCIe) bus, including a slot into which the NIC form-factor may removably engage. In another embodiment, NID 1720 is a network interface circuit laid out on a motherboard together with local link circuitry, processor interface circuitry, other input/output circuitry, memory circuitry, storage device and peripheral controller circuitry, and the like. In another embodiment, NID 1720 is a peripheral that interfaces with link 1708 via a peripheral input/output port such as a universal serial bus (USB) port. NID 1720 transmits and receives data over transmission medium 1726, which may be wired or wireless (e.g., radio frequency, infra-red or visible light spectra, etc.), fiber optics, or the like.

Figure 18:
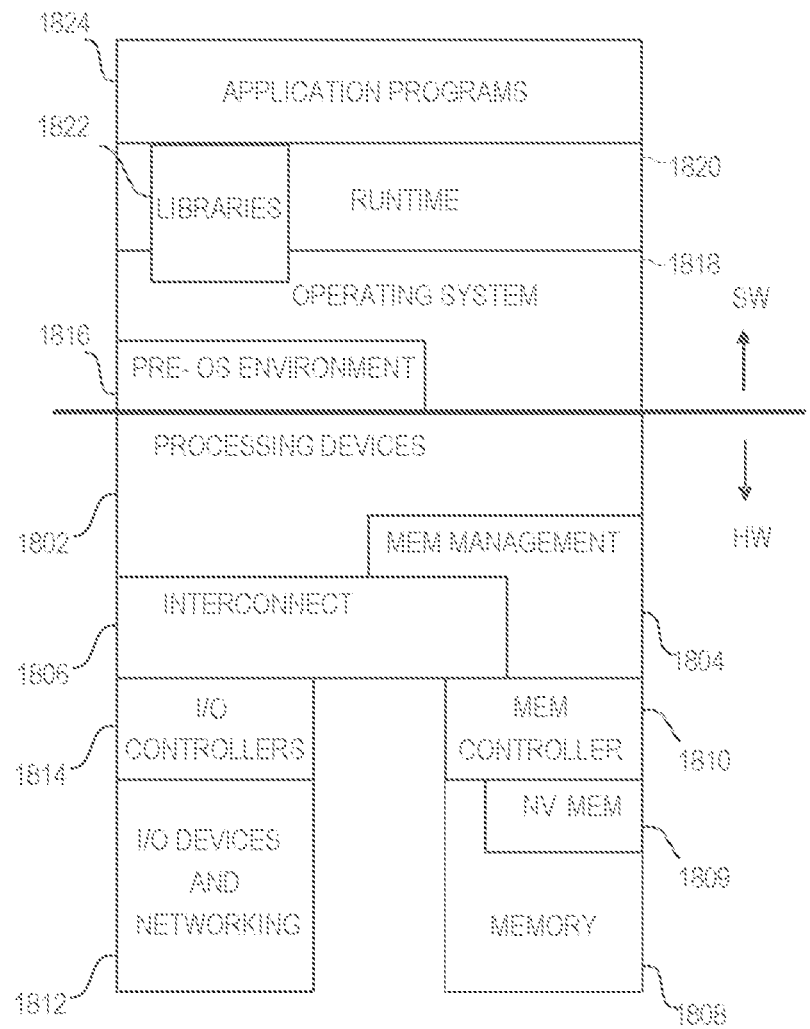
FIG. 18 is a diagram illustrating an exemplary hardware and software architecture of a computing device such as the one depicted in FIG. 17, in which various interfaces between hardware components and software components are shown.

FIG. 18 is a diagram illustrating an exemplary hardware and software architecture of a computing device such as the one depicted in FIG. 17, in which various interfaces between hardware components and software components are shown. As indicated by HW, hardware components are represented below the divider line, whereas software components denoted by SW reside above the divider line. On the hardware side, processing devices 1802 (which may include one or more microprocessors, digital signal processors, etc., each having one or more processor cores, are interfaced with memory management device 1804 and system interconnect 1806. Memory management device 1804 provides mappings between virtual memory used by processes being executed, and the physical memory. Memory management device 1804 may be an integral part of a central processing unit which also includes the processing devices 1802.

Interconnect 1806 includes a backplane such as memory, data, and control lines, as well as the interface with input/output devices, e.g., PCI, USB, etc. Memory 1808 (e.g., dynamic random access memory—DRAM) and non-volatile memory 1809 such as flash memory (e.g., electrically-erasable read-only memory—EEPROM, NAND Flash, NOR Flash, etc.) are interfaced with memory management device 1804 and interconnect 1806 via memory controller 1810. This architecture may support direct memory access (DMA) by peripherals in some embodiments. I/O devices, including video and audio adapters, non-volatile storage, external peripheral links such as USB, Bluetooth, etc., as well as network interface devices such as those communicating via Wi-Fi or LTE-family interfaces, are collectively represented as I/O devices and networking 1812, which interface with interconnect 1806 via corresponding I/O controllers 1814.

On the software side, a pre-operating system (pre-OS) environment 1816, which is executed at initial system start-up and is responsible for initiating the boot-up of the operating system. One traditional example of pre-OS environment 1816 is a system basic input/output system (BIOS). In present-day systems, a unified extensible firmware interface (UEFI) is implemented. Pre-OS environment 1816, is responsible for initiating the launching of the operating system, but also provides an execution environment for embedded applications according to certain aspects of the invention.

Operating system (OS) 1818 provides a kernel that controls the hardware devices, manages memory access for programs in memory, coordinates tasks and facilitates multi-tasking, organizes data to be stored, assigns memory space and other resources, loads program binary code into memory, initiates execution of the application program which then interacts with the user and with hardware devices, and detects and responds to various defined interrupts. Also, operating system 1818 provides device drivers, and a variety of common services such as those that facilitate interfacing with peripherals and networking, that provide abstraction for application programs so that the applications do not need to be responsible for handling the details of such common operations. Operating system 1818 additionally provides a graphical user interface (GUI) that facilitates interaction with the user via peripheral devices such as a monitor, keyboard, mouse, microphone, video camera, touchscreen, and the like.

Runtime system 1820 implements portions of an execution model, including such operations as putting parameters onto the stack before a function call, the behavior of disk input/output (I/O), and parallel execution-related behaviors. Runtime system 1820 may also perform support services such as type checking, debugging, or code generation and optimization.

Libraries 1822 include collections of program functions that provide further abstraction for application programs. These include shared libraries, dynamic linked libraries (DLLs), for example. Libraries 1822 may be integral to the operating system 1818, runtime system 1820, or may be added-on features, or even remotely-hosted. Libraries 1822 define an application program interface (API) through which a variety of function calls may be made by application programs 1824 to invoke the services provided by the operating system 1818. Application programs 1824 are those programs that perform useful tasks for users, beyond the tasks performed by lower-level system programs that coordinate the basis operability of the computing device itself.

Process Flow

Figure 20:
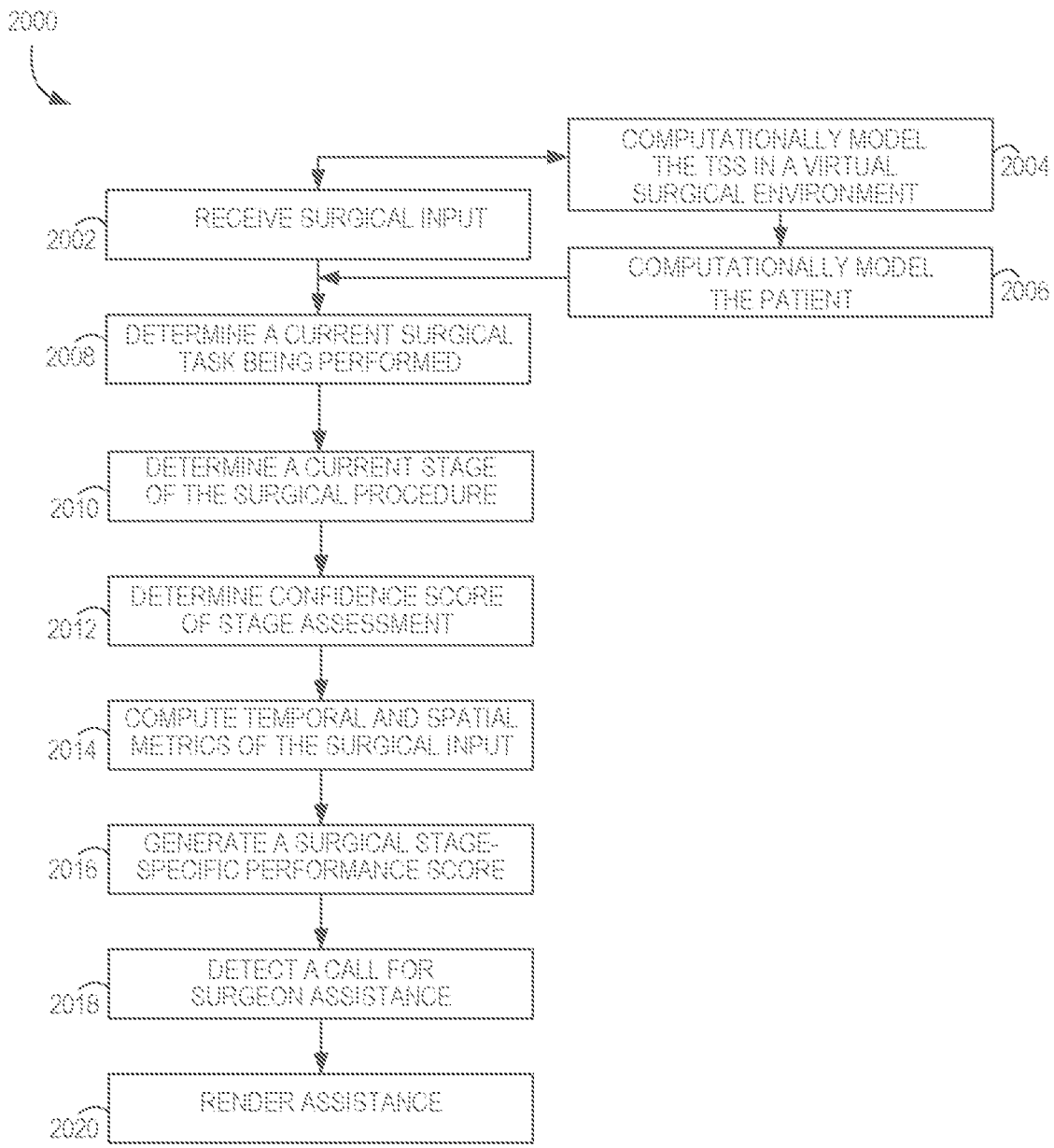
FIG. 20 is a process flow diagram illustrating an example method of operating a TSS support system such as the system of FIG. 9 according to some embodiments.

FIG. 20 is a process flow diagram illustrating an example method 200 of operating a TSS support system, such as system 900. It should be noted that method 2000 is a richly-featured embodiment that combines a variety of different operations for illustrative purposes. Although the example depicted in FIG. 20 may be a practical embodiment, it will be understood that in various other embodiments, certain operations may be modified, omitted, or re-ordered.

The following description references FIG. 20, along with the system and operational-component diagrams of FIGS. 9-16. At 2002, event monitor 1102 of surgical input assessor 1002 receives surgical input. The surgical input includes monitored events of the TSS. In addition, the surgical input may include control inputs to a computational model of the TSS in simulator 1006. The surgical input may also include modeled events from the computational model of the TSS.

At 2004, TSS modeler 1310 models a TSS in a virtual surgical environment. This may include computationally representing the tools, end effectors, and other configured portions, as defined in configuration information 1312. TSS modeler 1310 processes control inputs, and in the model effects virtual state changes in response to those control inputs. The virtual state changes may themselves constitute a type of event that event monitor 1102 may receive.

At 2006, patient model 1302 models the patient, including effects of the operation of the TSS modeler 1310. At 2008, surgical input assessor determines the current surgical task being performed. At 2010, segmenter 104 determines the current stage of the surgical procedure based on the surgical input and, optionally, on the assessed task.

At 2012, confidence measurement engine 1230 of segmenter 1004 determines the confidence score of the stage assessment. At 2014, surgeon assessor 908 computes the temporal and spatial metrics of the surgical input using surgical technique assessor 1402. Optionally, the confidence score is taken into account. At 2016 surgical technique assessor generates a stage-specific performance score for the surgeon or surgical staff.

At 2018, based on the current stage of the surgical procedure, on the performance score, or on some combination of these items, a call for surgeon assistance may be detected. The call for assistance may be provided by the surgeon or other operator. At 2020, stage-synchronized assistance is rendered.

Additional Notes and Examples

Example 1 is a surgery-support system for a teleoperated surgical system (TSS) that includes a surgeon input interface that accepts surgical control input for effecting an electro-mechanical surgical system to carry out a surgical procedure, the surgery-support system comprising: a virtual surgical environment engine including computing hardware operatively configured to implement: a surgical input assessor engine to receive surgical input including monitored events of the TSS; and a segmenter engine to determine a current stage of the surgical procedure based on the surgical input; and an assist engine including computing hardware operatively configured to implement: a TSS interface communicatively coupled to the surgeon input interface of the TSS; an assistance call detector to detect a call for surgeon assistance; and an assistance rendering engine to initiate context-relevant assistance via the TSS interface in response to the call for surgeon assistance, the context-relevant assistance being stage-synchronized with the surgical procedure.

In Example 2, the subject matter of Example 1 optionally includes the TSS.

In Example 3, the subject matter of any one or more of Examples 1-2 optionally include wherein the virtual surgical environment engine is further configured to implement a simulator engine to process a computational model of a surgical procedure based on the surgical input of the TSS.

In Example 4, the subject matter of Example 3 optionally includes wherein the simulator engine includes: a TSS model to computationally represent the TSS in the virtual surgical environment; and a patient model to computationally represent the patient based on the patient's physical characteristics, and changes to the patient effected by operation of the TSS model.

In Example 5, the subject matter of any one or more of Examples 3-4 optionally include wherein the simulator engine is configured to operate in parallel with an actual surgical procedure carried out via the TSS, wherein surgical control input to the TSS produces a virtual effect in the computational model of the simulator engine.

In Example 6, the subject matter of any one or more of Examples 3-5 optionally include wherein the surgical input received by the surgical input assessor engine includes simulated effects of the TSS control input from the computational model of the simulator engine.

In Example 7, the subject matter of any one or more of Examples 3-6 optionally include wherein the simulator engine is configured and initiated to simulate a specific stage of a surgical procedure based on a determination of the current stage.

In Example 8, the subject matter of any one or more of Examples 1-7 optionally include wherein the monitored events include TSS control input that controls an electromechanical surgical system of the TSS.

In Example 9, the subject matter of any one or more of Examples 1-8 optionally include wherein the monitored events include TSS control input that controls a simulation of an electromechanical surgical system of the TSS.

In Example 10, the subject matter of any one or more of Examples 1-9 optionally include wherein the monitored events include TSS-detected actions by a surgical assistant.

In Example 11, the subject matter of any one or more of Examples 1-10 optionally include wherein the segmenter engine includes a confidence measurement engine to determine a confidence score representing a probability of correct segmentation determination.

In Example 12, the subject matter of Example 11 optionally includes wherein the confidence score is indicative of suitability of a corresponding sequence of surgical input to train a deep-leaning engine of the segmenter engine.

In Example 13, the subject matter of any one or more of Examples 1-12 optionally include wherein the segmenter engine includes a real-time segmentation assessor configured to implement a trained neural network to process portions of the surgical input during the surgical procedure.

In Example 14, the subject matter of Example 13 optionally includes wherein the segmenter engine further includes a post-processing segmentation assessor configured to implement clustering algorithm to process portions of the surgical input.

In Example 15, the subject matter of any one or more of Examples 13-14 optionally include wherein the trained neural network is trained based on prior surgical input from a plurality of prior surgical procedures.

In Example 16, the subject matter of any one or more of Examples 13-15 optionally include wherein the trained neural network is trained based on prior surgical input from a plurality of prior-simulated surgical procedures.

In Example 17, the subject matter of any one or more of Examples 1-16 optionally include wherein the surgical input assessor engine includes a task assessor engine configured to determine a current surgical task being performed based on the surgical input, wherein the current surgical task comprises a series of events that produce a defined surgical effect; and wherein the segmenter engine is to determine a current stage of the surgical procedure based further on the current surgical task.

In Example 18, the subject matter of any one or more of Examples 1-17 optionally include a surgeon assessor engine including computing hardware operatively configured to implement: a surgical technique assessor engine configured to: access the surgical input and the current stage of the surgical procedure; compute a plurality of temporal and spatial metrics of the surgical input corresponding to a plurality of different stage of the surgical procedure including the current stage; and generate a surgical stage-specific performance score representing a quality of surgical performance of a surgeon producing the surgical control input.

In Example 19, the subject matter of Example 18 optionally includes wherein the surgical technique assessor is further configured to perform a comparison between the temporal and spatial metrics and benchmark metrics that are based on expertly-performed stages of the surgical procedure; and wherein the performance score is based on a result of the comparison.

In Example 20, the subject matter of any one or more of Examples 18-19 optionally include wherein the surgical technique assessor is further configured to: access a confidence score representing a probability of correct segmentation determination by the segmenter engine; and generate the performance score based further on the confidence score.

In Example 21, the subject matter of any one or more of Examples 18-20 optionally include wherein the performance score is a running score that is updated throughout the surgical procedure.

In Example 22, the subject matter of any one or more of Examples 18-21 optionally include wherein the assistance call detector is configured to detect the call for surgeon assistance based on the performance score.

In Example 23, the subject matter of any one or more of Examples 1-22 optionally include wherein the context-relevant assistance includes an expert video segment containing a demonstration of a stage-specific portion of the surgical procedure being carried out.

In Example 24, the subject matter of any one or more of Examples 1-23 optionally include wherein the context-relevant assistance includes a configuration and initiation of a stage-specific simulation of the surgical procedure.

In Example 25, the subject matter of any one or more of Examples 1-24 optionally include wherein the context-relevant assistance includes adjustment of control settings.

Example 26 is a machine-implemented method for supporting a teleoperated surgical system (TSS) that includes a surgeon input interface that accepts surgical control input for effecting an electromechanical surgical system to carry out a surgical procedure, the method comprising: receiving surgical input including monitored events of the TSS; determining a current stage of the surgical procedure based on the surgical input; detecting a call for surgeon assistance; and initiating context-relevant assistance to the surgeon input interface in response to the call for surgeon assistance, the context-relevant assistance being stage-synchronized with the surgical procedure.

In Example 27, the subject matter of Example 26 optionally includes simulating the surgical procedure as a computational model based on the surgical input of the TSS.

In Example 28, the subject matter of Example 27 optionally includes wherein simulating the surgical procedure includes, computationally representing the TSS in a virtual surgical environment as part of the computational model; and computationally representing the patient based on the patient's physical characteristics, and changes to the patient effected by modeled operation of the computationally-represented TSS in the computational model.

In Example 29, the subject matter of any one or more of Examples 27-28 optionally include wherein the simulating is conducted in parallel with an actual surgical procedure carried out via the TSS, wherein surgical control input to the TSS produces a virtual effect in the computational model.

In Example 30, the subject matter of any one or more of Examples 27-29 optionally include wherein the surgical input includes simulated effects of the TSS control input from the computational model.

In Example 31, the subject matter of any one or more of Examples 27-30 optionally include simulating a specific stage of the surgical procedure using the computational model based on a determination of the current stage.

In Example 32, the subject matter of any one or more of Examples 26-31 optionally include wherein the monitored events include TSS control input that controls an electromechanical surgical system of the TSS.

In Example 33, the subject matter of any one or more of Examples 26-32 optionally include wherein the monitored events include TSS control input that controls a simulation of an electromechanical surgical system of the TSS.

In Example 34, the subject matter of any one or more of Examples 26-33 optionally include wherein the monitored events include TSS-detected actions by a surgical assistant.

In Example 35, the subject matter of any one or more of Examples 26-34 optionally include determining a confidence score representing a probability of correct segmentation determination.

In Example 36, the subject matter of Example 35 optionally includes wherein the confidence score is indicative of suitability of a corresponding sequence of surgical input to train a deep-learning algorithm.

In Example 37, the subject matter of any one or more of Examples 26-36 optionally include wherein in determining the current stage of the surgical procedure, a trained neural network is implemented to process portions of the surgical input during the surgical procedure.

In Example 38, the subject matter of Example 37 optionally includes wherein in determining the current stage of the surgical procedure, a clustering algorithm is implemented to process portions of the surgical input.

In Example 39, the subject matter of any one or more of Examples 37-38 optionally include wherein the trained neural network is trained based on prior surgical input from a plurality of prior surgical procedures.

In Example 40, the subject matter of any one or more of Examples 37-39 optionally include wherein the trained neural network is trained based on prior surgical input from a plurality of prior-simulated surgical procedures.

In Example 41, the subject matter of any one or more of Examples 26-40 optionally include determining a current surgical task being performed based on the surgical input, wherein the current surgical task comprises a series of events that produce a defined surgical effect; and wherein the determining of the current stage of the surgical procedure is based further on the current surgical task.

In Example 42, the subject matter of any one or more of Examples 26-41 optionally include computing a plurality of temporal and spatial metrics of the surgical input corresponding to a plurality of different stage of the surgical procedure including the current stage, and generating a surgical stage-specific performance score representing a quality of surgical performance of a surgeon producing the surgical control input.

In Example 43, the subject matter of Example 42 optionally includes performing a comparison between the temporal and spatial metrics, and benchmark metrics that are based on expertly-performed stages of the surgical procedure; wherein the performance score is based on a result of the comparison.

In Example 44, the subject matter of any one or more of Examples 42-43 optionally include generating the performance score based further on the confidence score representing a probability of correct segmentation determination.

In Example 45, the subject matter of any one or more of Examples 42-44 optionally include wherein the performance score is a running score that is updated throughout the surgical procedure.

In Example 46, the subject matter of any one or more of Examples 42-45 optionally include wherein the call for surgeon assistance is based on the performance score.

In Example 47, the subject matter of any one or more of Examples 26-46 optionally include wherein the context-relevant assistance includes an expert video segment containing a demonstration of a stage-specific portion of the surgical procedure being carried out.

In Example 48, the subject matter of any one or more of Examples 26-47 optionally include wherein the context-relevant assistance includes a configuration and initiation of a stage-specific simulation of the surgical procedure.

In Example 49, the subject matter of any one or more of Examples 26-48 optionally include wherein the context-relevant assistance includes adjustment of control settings.

Example 50 is at least one non-transitory machine-readable storage medium containing instructions that, when executed on a computing platform, cause the computing platform to implement a special-purpose machine for supporting a teleoperated surgical system (TSS) that includes a surgeon input interface that accepts surgical control input for effecting an electromechanical surgical system to carry out a surgical procedure, the instructions comprising: instructions for receiving surgical input including monitored events of the TSS; instructions for determining a current stage of the surgical procedure based on the surgical input; instructions for detecting a call for surgeon assistance, and instructions for initiating context-relevant assistance to the surgeon input interface in response to the call for surgeon assistance, the context-relevant assistance being stage-synchronized with the surgical procedure.

In Example 51, the subject matter of Example 50 optionally includes instructions for simulating the surgical procedure as a computational model based on the surgical input of the TSS.

In Example 52, the subject matter of Example 51 optionally includes wherein the instructions for simulating the surgical procedure include: instructions for computationally representing the TSS in a virtual surgical environment as part of the computational model; and instructions for computationally representing the patient based on the patient's physical characteristics, and changes to the patient effected by modeled operation of the computationally-represented TSS in the computational model.

In Example 53, the subject matter of any one or more of Examples 51-52 optionally include wherein the simulating is to be conducted in parallel with an actual surgical procedure carried out via the TSS, wherein surgical control input to the TSS produces a virtual effect in the computational model.

In Example 54, the subject matter of any one or more of Examples 51-53 optionally include wherein the surgical input includes simulated effects of the TSS control input from the computational model.

In Example 55, the subject matter of any one or more of Examples 51-54 optionally include instructions for simulating a specific stage of the surgical procedure using the computational model based on a determination of the current stage.

In Example 56, the subject matter of any one or more of Examples 50-55 optionally include wherein the monitored events include TSS control input that controls an electromechanical surgical system of the TSS.

In Example 57, the subject matter of any one or more of Examples 50-56 optionally include wherein the monitored events include TSS control input that controls a simulation of an electromechanical surgical system of the TSS.

In Example 58, the subject matter of any one or more of Examples 50-57 optionally include wherein the monitored events include TSS-detected actions by a surgical assistant.

In Example 59, the subject matter of any one or more of Examples 50-58 optionally include instructions for determining a confidence score representing a probability of correct segmentation determination.

In Example 60, the subject matter of Example 59 optionally includes wherein the confidence score is indicative of suitability of a corresponding sequence of surgical input to train a deep-learning algorithm.

In Example 61, the subject matter of any one or more of Examples 50-60 optionally include wherein the instructions for determining the current stage of the surgical procedure, cause a trained neural network to be implemented to process portions of the surgical input during the surgical procedure.

In Example 62, the subject matter of Example 61 optionally includes wherein the instructions for determining the current stage of the surgical procedure, cause a clustering algorithm to be implemented to process portions of the surgical input.

In Example 63, the subject matter of any one or more of Examples 61-62 optionally include wherein the trained neural network is trained based on prior surgical input from a plurality of prior surgical procedures.

In Example 64, the subject matter of any one or more of Examples 61-63 optionally include wherein the trained neural network is trained based on prior surgical input from a plurality of prior-simulated surgical procedures.

In Example 65, the subject matter of any one or more of Examples 50-64 optionally include instructions for determining a current surgical task being performed based on the surgical input, wherein the current surgical task comprises a series of events that produce a defined surgical effect; and wherein the instructions for determining of the current stage of the surgical procedure base the determining on the current surgical task.

In Example 66, the subject matter of any one or more of Examples 50-65 optionally include instructions for computing a plurality of temporal and spatial metrics of the surgical input corresponding to a plurality of different stage of the surgical procedure including the current stage; and instructions for generating a surgical stage-specific performance score representing a quality of surgical performance of a surgeon producing the surgical control input.

In Example 67, the subject matter of Example 66 optionally includes instructions for performing a comparison between the temporal and spatial metrics, and benchmark metrics that are based on expertly-performed stages of the surgical procedure; wherein the performance score is based on a result of the comparison.

In Example 68, the subject matter of any one or more of Examples 66-67 optionally include instructions for generating the performance score based further on the confidence score representing a probability of correct segmentation determination.

In Example 69, the subject matter of any one or more of Examples 66-68 optionally include wherein the performance score is a running score that is updated throughout the surgical procedure.

In Example 70, the subject matter of any one or more of Examples 66-69 optionally include wherein the call for surgeon assistance is based on the performance score.

In Example 71, the subject matter of any one or more of Examples 50-70 optionally include wherein the context-relevant assistance includes an expert video segment containing a demonstration of a stage-specific portion of the surgical procedure being carried out.

In Example 72, the subject matter of any one or more of Examples 50-71 optionally include wherein the context-relevant assistance includes a configuration and initiation of a stage-specific simulation of the surgical procedure.

In Example 73, the subject matter of any one or more of Examples 50-72 optionally include wherein the context-relevant assistance includes adjustment of control settings.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A surgery-support system for a teleoperated surgical system (BS) that includes a user input interface that accepts control input from a user for effecting an electromechanical surgical system to carry out a surgical procedure, the surgery-support system comprising:
   a segmenter engine to determine a current stage of the surgical procedure based on the surgical control input; and
   an assist engine including computing hardware operatively configured to implement:
   a TSS interface communicatively coupled to the user input interface of the TSS;
   an assistance call detector to detect a call for user assistance; and
   an assistance rendering engine that includes a control settings adjuster to adjust a control setting to automatically vary one or more behaviors of the TSS assistance via the TSS interface in response to a call for user assistance;
   a user assessor engine including computing hardware operatively configured to implement:
   access camera control input and;
   compute spatial metrics of camera control input; and generate a camera performance score representing a quality of camera control of a user providing the camera control input;

wherein the control settings adjuster initiates adjustment of a camera control setting in response to the call for user assistance based at least in part upon the camera performance score.

2. The method of claim 1, wherein the adjustment includes at least one of change in horizon orientation of a visual display of a surgical scene, change of two-dimensional region shown within a visual display of a surgical scene and change of a zoom level of a visual display of a surgical scene.

3. A machine-implemented method for supporting a tele-operated surgical system (TSS) that includes a surgeon input interface that accepts surgical control input from a user for effecting an electromechanical surgical system to carry out a surgical procedure, the method comprising:

determining a current stage of the surgical procedure based on the user control input; and adjusting a control setting to automatically vary one or more behaviors of the TSS interface in response to a call for user assistance;

accessing camera control input and;

computing spatial metrics of camera control input; and generating a camera performance score representing a quality of camera control of a user providing the camera control input;

detecting a call for user assistance;

adjusting a camera control setting in response to the call for user assistance based at least in part upon the camera performance score.

4. The method of claim 3, wherein the adjusting includes at least one of changing horizon orientation of a visual display of a surgical scene, changing two-dimensional region shown within a visual display of a surgical scene and changing a zoom level of a visual display of a surgical scene.

* * * * *

UNITED STATES PATENT AND TRADEMARK OFFICE
CERTIFICATE OF CORRECTION

| | |
|---|---|
| PATENT NO. | : 11,751,957 B2 |
| APPLICATION NO. | : 17/137342 |
| DATED | : September 12, 2023 |
| INVENTOR(S) | : Anthony M. Jarc and Chi Zhang |

It is certified that error appears in the above-identified patent and that said Letters Patent is hereby corrected as shown below:

In the Claims

At Claim 1, Column 36, Line 46, delete "(BS)" and insert --(TSS)--

Signed and Sealed this
Seventeenth Day of October, 2023

Katherine Kelly Vidal
*Director of the United States Patent and Trademark Office*